US011077306B2

(12) United States Patent
Grenz et al.

(10) Patent No.: US 11,077,306 B2
(45) Date of Patent: Aug. 3, 2021

(54) HEART RATE BASED CONTROL OF CARDIAC RESYNCHRONIZATION THERAPY

(71) Applicant: Medtronic, Inc., Minneapolis, MN (US)

(72) Inventors: Nathan A. Grenz, Shoreview, MN (US); Thomas J. Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 860 days.

(21) Appl. No.: 15/418,046

(22) Filed: Jan. 27, 2017

(65) Prior Publication Data
US 2018/0214695 A1 Aug. 2, 2018

(51) Int. Cl.
*A61N 1/368* (2006.01)
*A61N 1/37* (2006.01)
*A61N 1/362* (2006.01)
*A61N 1/365* (2006.01)

(52) U.S. Cl.
CPC ........... *A61N 1/3684* (2013.01); *A61N 1/368* (2013.01); *A61N 1/3627* (2013.01); *A61N 1/3682* (2013.01); *A61N 1/36514* (2013.01); *A61N 1/371* (2013.01)

(58) Field of Classification Search
CPC combination set(s) only.
See application file for complete search history.

(56) References Cited

U.S. PATENT DOCUMENTS

| 4,374,382 A | 2/1983 | Markowitz |
| 5,117,824 A | 6/1992 | Keimel et al. |
| 5,340,361 A | 8/1994 | Sholder |
| 5,545,182 A | 8/1996 | Stotts et al. |
| 5,545,186 A | 8/1996 | Olson et al. |

(Continued)

FOREIGN PATENT DOCUMENTS

| EP | 2398554 A1 | 12/2011 |
| WO | 2006069032 A1 | 6/2006 |

OTHER PUBLICATIONS

Written Opinion of International Application No. PCT/US2018/014982, dated Aug. 2, 2018, 5 pp.

(Continued)

*Primary Examiner* — Rex R Holmes
*Assistant Examiner* — Jennifer L Ghand
(74) *Attorney, Agent, or Firm* — Shumaker & Sieffert, P.A.

(57) ABSTRACT

In some examples, controlling delivery of cardiac resynchronization therapy (CRT) includes storing, in a memory of an implantable medical device system and in association with each of a plurality of heart rates, at least one respective value for an interval between an atrial event and a ventricular event. Processing circuitry of the implantable medical device system may determine a heart rate of a patient and select one of the stored values for the interval between the atrial event and the ventricular event associated with the determined heart rate. The processing circuitry may further determine whether to control therapy delivery circuitry of the implantable medical device system to deliver fusion pacing or biventricular pacing, based on the selected one of the stored values for the interval between the atrial event and the ventricular event.

11 Claims, 9 Drawing Sheets

(56) References Cited

U.S. PATENT DOCUMENTS

| | | | |
|---|---|---|---|
| 5,755,736 | A | 5/1998 | Gillberg et al. |
| 6,766,197 | B1 | 7/2004 | Levine |
| 6,871,096 | B2 | 3/2005 | Hill |
| 6,928,326 | B1 | 8/2005 | Levine |
| 7,079,896 | B1 | 7/2006 | Park et al. |
| 7,181,284 | B2 | 2/2007 | Burnes |
| 7,181,286 | B2 | 2/2007 | Sieracki et al. |
| 7,561,914 | B2 | 7/2009 | Busacker et al. |
| 7,706,879 | B2 | 4/2010 | Burnes et al. |
| 7,881,791 | B2 | 2/2011 | Sambelashvili et al. |
| 7,930,027 | B2 | 4/2011 | Prakash et al. |
| 7,941,218 | B2 | 5/2011 | Sambelashvili et al. |
| 8,121,685 | B2 | 2/2012 | Ding et al. |
| 8,886,307 | B2 | 11/2014 | Sambelashvili et al. |
| 9,220,905 | B2 | 12/2015 | Munsterman et al. |
| 2003/0083700 | A1 | 5/2003 | Hill |
| 2005/0131476 | A1 | 6/2005 | Kim et al. |
| 2005/0137632 | A1 | 6/2005 | Ding et al. |
| 2005/0209648 | A1 | 9/2005 | Burnes et al. |
| 2006/0224198 | A1 | 10/2006 | Dong et al. |
| 2006/0259086 | A1* | 11/2006 | Yu .................. A61N 1/3627 607/9 |
| 2006/0287685 | A1 | 12/2006 | Meyer et al. |
| 2007/0179542 | A1* | 8/2007 | Prakash ............ A61N 1/3627 607/9 |
| 2007/0191892 | A1 | 8/2007 | Mullen et al. |
| 2008/0269816 | A1 | 10/2008 | Prakash et al. |
| 2008/0269823 | A1 | 10/2008 | Burnes et al. |
| 2008/0280341 | A1 | 11/2008 | KenKnight et al. |
| 2009/0234411 | A1 | 9/2009 | Sambelashvili et al. |
| 2009/0234412 | A1 | 9/2009 | Sambelashvili |
| 2009/0234413 | A1 | 9/2009 | Sambelashvili et al. |
| 2009/0234414 | A1 | 9/2009 | Sambelashvilli et al. |
| 2009/0234415 | A1 | 9/2009 | Sambelashvili et al. |
| 2009/0248103 | A1 | 10/2009 | Sambelashvili et al. |
| 2010/0016914 | A1 | 1/2010 | Mullen et al. |
| 2010/0114232 | A1 | 5/2010 | Min |
| 2010/0198291 | A1 | 8/2010 | Sambelashvili et al. |
| 2010/0234916 | A1 | 9/2010 | Turcott et al. |
| 2010/0286541 | A1 | 11/2010 | Musley et al. |
| 2010/0305646 | A1 | 12/2010 | Schulte et al. |
| 2011/0190841 | A1 | 8/2011 | Sambelashvili et al. |
| 2011/0196440 | A1 | 8/2011 | Koh |
| 2011/0196444 | A1 | 8/2011 | Prakash et al. |
| 2012/0158088 | A1 | 6/2012 | Kramer et al. |
| 2013/0030489 | A1 | 1/2013 | Munsterman et al. |
| 2013/0197599 | A1 | 8/2013 | Sambelashvili et al. |
| 2014/0277233 | A1 | 9/2014 | Ghosh |
| 2016/0051823 | A1 | 2/2016 | Maile et al. |
| 2016/0213928 | A1 | 7/2016 | Ghosh |
| 2017/0106191 | A1 | 4/2017 | Pei |
| 2018/0361150 | A1 | 12/2018 | Ternes et al. |
| 2018/0361161 | A1 | 12/2018 | Ternes et al. |
| 2018/0361162 | A1 | 12/2018 | Ternes et al. |

OTHER PUBLICATIONS

Daubert et al., "2012 EHRA/HRS Expert Consensus Statement on Cardiac Resynchronization Therapy in Heart Failure: Implant and Follow-Up Recommendations and Management", Heart Rhythm, vol. 9, No. 9, Sep. 2012, pp. 1524-1576.

Ellenbogen et al., "Primary Results From the SmartDelay Determined AV Optimization: A Comparison to Other AV Delay Methods Used in Cardiac Resynchronization Therapy (SMART-AV) Trial", Circulation, http://circ.ahajournals.org/content/early/2010/11/12/CIRCULATIONAHA 110.992552, Nov. 12, 2010, 19 pp.

(PCT/US2018/014982) PCT Notification of Transmittal of the International Search Report and the Written Opinion of the International Searching Authority, dated Apr. 4, 2018, 6 pages.

Khaykin et al., "Adjusting the timing of left-ventricular pacing using electrocardiogram and device electrograms," Europace doi: 10.1093/europace/eur146, May 19, 2011, 7 pp.

* cited by examiner

HEART RATE BASED CONTROL OF CARDIAC RESYNCHRONIZATION THERAPY

TECHNICAL FIELD

The disclosure relates generally to medical device systems and, more particularly, cardiac therapy delivery by implantable medical devices.

BACKGROUND

Some types of implantable medical devices, such as cardiac pacemakers or implantable cardioverter defibrillators, provide therapeutic electrical stimulation to a heart of a patient via electrodes of one or more implantable leads. The therapeutic electrical stimulation may be delivered to the heart in the form of pulses or shocks for pacing, cardioversion or defibrillation. In some cases, an implantable medical device may sense intrinsic depolarizations of the heart, and control the delivery of therapeutic stimulation to the heart based on the sensing.

Cardiac resynchronization therapy (CRT) is one type of therapy delivered by an implantable medical device. Cardiac resynchronization therapy may help enhance cardiac output by resynchronizing the electromechanical activity of the ventricles of the heart. Ventricular desynchrony may occur in patients that suffer from congestive heart failure (CHF).

SUMMARY

In general, this disclosure is directed to techniques for controlling the delivery of CRT. Such techniques may include determining an interval between an atrial event and a ventricular event of a patient, and determining whether to deliver fusion pacing therapy, i.e., CRT pacing delivered to one of the ventricles, such as the left ventricle, or biventricular pacing therapy to the patient based on the determined interval. In some examples, the value of an interval between the atrial event and the ventricular event, e.g., an intrinsic ventricular event, may be obtained by periodically suspending the delivery of therapy and determining the current value of the interval.

However, the act of suspending the delivery of therapy and determining a current value of the interval may result in a loss of delivery of CRT pacing to the patient. Since increased CRT pacing may be associated with improved patient outcome, it therefore may be desirable to decrease the frequency at which the current value of the interval between the atrial event and the ventricular event is determined. Accordingly, techniques described herein may include determining a heart rate of a patient and selecting from a table, based on the heart rate, a respective value for the interval between the atrial event and the ventricular event. In this manner, the interval to be used for determining whether to apply fusion pacing therapy or biventricular pacing therapy may be obtained without suspending the delivery of therapy. In techniques described herein, the suspension of the delivery of therapy to determine the current value of the interval thus may be limited to relatively infrequent occasions, such periodic updates to the table.

In one example, a method for controlling delivery of cardiac resynchronization therapy (CRT) comprises storing, in a memory of an implantable medical device system and in association with each of a plurality of heart rates, at least one respective value for an interval between an atrial event and a ventricular event; and by processing circuitry of the implantable medical device system: determining a heart rate of a patient; selecting one of the stored values for the interval between the atrial event and the ventricular event associated with the determined heart rate; and determining whether to control therapy delivery circuitry of the implantable medical device system to deliver fusion pacing or biventricular pacing based on the selected one of the stored values for the interval between the atrial event and the ventricular event.

In another example, a system for controlling delivery of cardiac resynchronization therapy (CRT) comprises therapy delivery circuitry configured to deliver cardiac resynchronization pacing therapy to a heart of a patient; sensing circuitry configured to sense electrical activity of the heart; memory configured to store, in association with each of a plurality of heart rates, at least one respective value for an interval between the atrial event and the ventricular event; and processing circuitry configured to: determine the heart rate of a patient based on the electrical activity sensed by the sensing circuitry; select one of the stored values for the interval between the atrial event and the ventricular event associated with the determined heart rate; and determine whether to control the therapy delivery circuitry to deliver fusion pacing or biventricular pacing based on the selected one of the stored values for the interval between the atrial event and the ventricular event.

In another example, an implantable medical device (IMD) configured to deliver cardiac resynchronization therapy (CRT) to a patient comprises a housing configured for implantation within the patient; therapy delivery circuitry disposed within the housing and configured to deliver cardiac resynchronization pacing therapy to a heart of the patient; sensing circuitry disposed within the housing and configured to sense electrical activity of the heart; memory disposed within the housing and configured to store, in association with each of a plurality of heart rates, at least one respective value for the interval between the atrial event and the ventricular event; and processing circuitry disposed within the housing and configured to: determine a first heart rate of a patient for at least one preceding cardiac cycle based on the sensed electrical activity; select one of the stored values for the interval between the atrial event and the ventricular event associated with the determined first heart rate; and determine whether to control the therapy delivery circuitry to deliver fusion pacing or biventricular pacing for a current cardiac cycle based on the selected one of the stored values for the interval between the atrial event and the ventricular event, wherein the processing circuitry is further configured to periodically, the period being greater than a cardiac cycle: determine a second heart rate of a patient based on the sensed electrical activity select one of the stored values for the interval between the atrial event and the ventricular event associated with the determined second heart rate; suspend the delivery of CRT; while the delivery of CRT is suspended, measure a current value of the interval between the atrial event and the ventricular event; compare the current value of the interval to the selected value of the interval; and update at least the selected value of the interval associated with the determined heart rate in the memory based on the comparison.

In another example, a system for controlling delivery of cardiac resynchronization therapy (CRT) comprises means for storing, in association with each of a plurality of heart rates, at least one respective value for an interval between an atrial event and a ventricular event; means for determining a heart rate of a patient; means for selecting one of the stored values for the interval between the atrial event and the ventricular event associated with the determined heart rate;

and means for determining whether to control therapy delivery circuitry of the implantable medical device system to deliver fusion pacing or biventricular pacing based on the selected one of the stored values for the interval between the atrial event and the ventricular event.

In another example, a non-transitory computer-readable medium storing instructions for causing processing circuitry of an implantable medical device system to perform a method for controlling delivery of cardiac resynchronization therapy (CRT), the method comprising storing, in a memory of the implantable medical device system and in association with each of a plurality of heart rates, at least one respective value for an interval between an atrial event and a ventricular event; determining a heart rate of a patient; selecting one of the stored values for the interval between the atrial event and the ventricular event associated with the determined heart rate; and determining whether to control therapy delivery circuitry of the implantable medical device system to deliver fusion pacing or biventricular pacing based on the selected one of the stored values for the interval between the atrial event and the ventricular event.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

Figure 1:
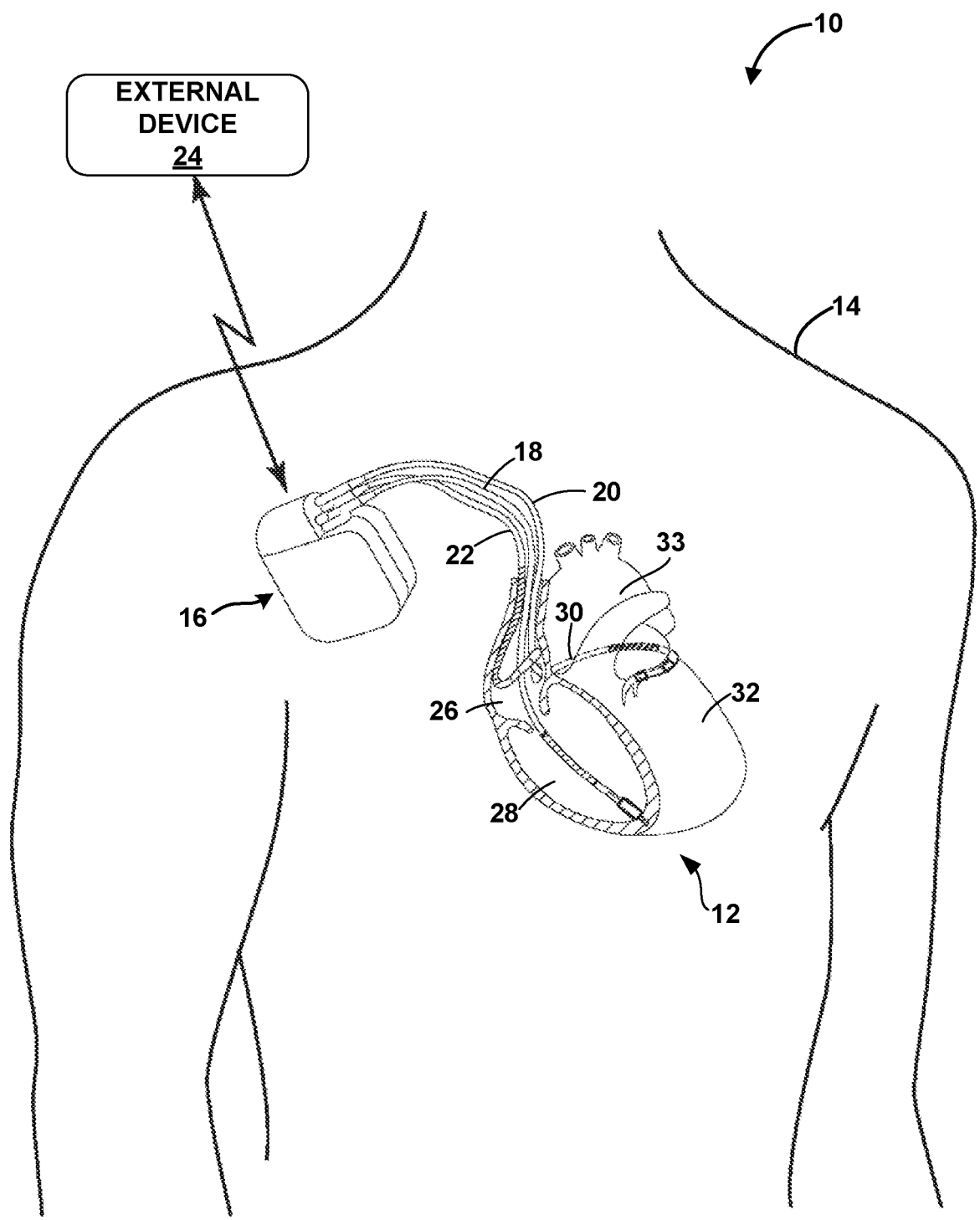
FIG. 1 is conceptual diagram illustrating an example medical device system.

In general, this disclosure describes example techniques related to controlling the delivery of cardiac resynchronization therapy (CRT) to a patient. For each of a plurality of heart rates, a memory, e.g., of an implantable medical device or an external computing device, stores one or more associated values of an interval between an atrial event and a ventricular event, e.g., an A-V interval, determined for the patient. In some examples, the ventricular event is a sensed or intrinsic ventricular event, and the interval is an $A-V_s$ interval. In some examples, the memory stores values for both of an interval between a sensed atrial event and the ventricular event, e.g., an $A_s-V_s$ interval, and an interval between a paced atrial event and the ventricular event, e.g., an $A_P-V_s$ interval. The values stored for the patient in the memory may be determined by monitoring the A-V conduction of the patient prior to, or during a suspension of, delivery of CRT.

To control the delivery of CRT by the implantable medical device, processing circuitry, e.g., of the implantable medical device or the external computing device, may determine the heart rate of the patient, and select the respective value for the A-V interval from the memory. The processing circuitry may control the delivery of CRT based on the selected value of the A-V interval. For example, the processing circuitry may determine whether to control therapy delivery circuitry of the implantable medical device to deliver fusion pacing, e.g., left-ventricular pacing, or biventricular pacing to the patient based on the selected A-V interval value. In examples in which the A-V interval value selected based on the heart rate is an $A-V_s$ interval value, the processing circuitry may further determine, based on the selected $A-V_s$ value, an $A-V_P$ interval value for timing the delivery of the fusion or biventricular pacing.

It is further contemplated that, in some examples, the A-V interval values stored in association with heart rates in the memory may be validated and, if necessary, updated periodically. In some examples, the processing circuitry may validate and/or update the stored A-V interval values by suspending the delivery of CRT, and measuring a current value of the A-V interval while delivery of CRT is suspended. Suspending the delivery of CRT may refer to, as examples, withholding ventricular pacing for one or more cardiac cycles, increasing an $A-V_P$ delay sufficiently so that intrinsic ventricular conduction may be observed, or pacing one ventricle at a sufficiently long $A-V_P$ delay and measuring intrinsic conduction on the other ventricle. The processing circuitry may compare the currently measured value of the interval to the value associated with the current heart rate. If the values are not sufficiently similar, the processing circuitry may modify the stored value based on the currently measured value, e.g., by replacing the stored A-V interval value with the currently measured value.

In some medical devices configured to provide adaptive CRT, a pacing configuration, e.g., a fusion pacing configuration or a biventricular pacing configuration, and timing of the pacing stimuli based on periodic intrinsic conduction measurements may be periodically adjusted to achieve more efficient physiologic pacing and to improve hemodynamics of the patient. Fusion pacing and biventricular pacing are described in further detail below. While the pacing stimuli may be pacing pulses or continuous time signals, the pacing stimuli are primarily referred to herein as pacing pulses for ease of description.

Fusion-based CRT (also referred to herein as fusion pacing) may be useful for restoring a depolarization sequence of a heart of a patient, which may be irregular due to ventricular dysfunction, in patients with preserved intrinsic atrial-ventricular (AV) conduction. In a fusion pacing configuration, a medical device delivers one or more fusion pacing pulses to one of the ventricles, and not the other. In particular, the medical device delivers the one or more fusion pacing pulses to a later-contracting ventricle (V2) in order to pre-excite the V2 and synchronize the depolarization of the V2 with the depolarization of the earlier contracting ventricle (V1). The ventricular activation of the V2 may "fuse" (or "merge") with the ventricular activation of the V1 that is attributable to intrinsic conduction of the heart. In this way, the intrinsic and pacing-induced excitation wave fronts may fuse together such that the depolarization of the V2 is resynchronized with the depolarization of the V1.

The medical device may be configured to deliver the fusion pacing pulse to the V2 according to a fusion pacing interval, which indicates the time relative to an atrial pace or sense event at which the fusion pacing pulse should be delivered to the V2. An atrial sense event may be, for example, a P wave of a sensed electrical cardiac signal and an atrial pacing event may be, for example, the time at which a stimulus is delivered to the atrium.

In some examples, the right ventricle (RV) may be the V1 and the left ventricle (LV) may be the V2. In other examples, the LV may be the V1 while the RV may be the V2. While the disclosure primarily refers to examples in which the first depolarizing ventricle V1 is the RV and the later depolarizing ventricle V2 is the LV, the devices, systems, techniques described herein for providing CRT may also apply to examples in which the first depolarizing ventricle V1 is the LV and the later depolarizing ventricle V2 is the RV.

In some fusion pacing techniques, a pacing pulse to the V2 ($V2_P$) is delivered upon expiration of a fusion pacing interval that is determined based on the intrinsic depolarization of the V1, which may be indicated by a sensing of ventricular activation ($V1_S$). Ventricular activation may be indicated by, for example, an R-wave of a sensed electrical cardiac signal. An example of a fusion pacing technique that times the delivery of the V2 pacing pulse ($V2_P$) to the intrinsic depolarization of the V1 is described in U.S. Pat. No. 7,181,286 to Burnes et al., which is entitled, "APPARATUS AND METHODS OF ENERGY EFFICIENT, ATRIAL-BASED BI-VENTRICULAR FUSION-PACING," and issued on Feb. 20, 2007. U.S. Pat. No. 7,181,286 to Burnes et al. is incorporated herein by reference in its entirety.

In one example disclosed by U.S. Pat. No. 7,181,286 to Burnes et al., a pacing pulse to the V2 ($V2_P$) is delivered a predetermined period of time following an atrial pace or sense event ($A_{P/S}$), where the predetermined period of time is substantially equal to the duration of time between the atrial pace or sense event ($A_{P/S}$) and a V1 sensing event ($V1_S$) of at least one prior cardiac cycle decremented by a duration of time referred to as the pre-excitation interval (PEI). Thus, one example equation that may be used to determine a fusion pacing interval ($A_{P/S}-V2_P$):

$$A_{P/S}-V2_P=(A_{P/S}-V1_S)-\text{PEI} \qquad \text{Equation (1)}$$

A cardiac cycle may include, for example, the time between the beginning of one heart beat to the next heartbeat. The duration of time between the atrial pace or sense event ($A_{P/S}$) and a V1 sensing event ($V1_S$) may be, for example, a measurement of intrinsic AV conduction time from an atrium to the first contracting ventricle of the heart of the patient. The PEI may indicate the amount of time with which a V2 pacing pulse precedes a V1 sensing event in order to achieve the fusing of the electromechanical performance of the V1 and V2. That is, the PEI may indicate the amount of time from the delivery of the V2 pacing pulse that is required to pre-excite the V2, such that the electromechanical performance of V1 and V2 merge into a fusion event. In some examples, the PEI is automatically determined by a medical device delivering the pacing therapy, e.g., based on determined intrinsic conduction times, while in other examples, the PEI may be predetermined by a clinician. In some examples, the PEI is a programmed value (e.g., about one millisecond (ms) to about 250 ms or more, such as about 100 ms to about 200 ms, or about 10 ms to about 40 ms) or is an adaptive value, such as about 10% of a measured intrinsic A–V2 conduction interval or measured intrinsic A–A cycle length.

The magnitude of the PEI may differ based on various factors, such as the heart rate of the patient, a dynamic physiologic conduction status of the heart of the patient, which may change based upon the physiological condition of the patient (e.g., ischemia status, myocardial infarction status, and so forth), as well as factors related to the therapy system, such as the location of sensing electrodes of the leads of the therapy system, the location of the pacing electrodes of the therapy system, and internal circuitry processing delays of the medical device.

Another technique for determining the timing of the delivery of a pacing pulse to a later depolarizing ventricle (V2) (which is sometimes also referred to as a "fusion pacing interval") is described in U.S. Patent Application Publication No. 2010/0198291 by Sambelashvili et al., which is incorporated herein by reference in its entirety. In some examples described by U.S. Patent Application Publication No. 2010/0198291 by Sambelashvili et al., the timing of the delivery of a pacing pulse is based on a depolarization of the V2 in at least one prior cardiac cycle. The depolarization of the V2 may be detected by sensing an event in the V2 ($V2_S$), such as an R-wave of an electrical cardiac signal. The V2 pacing pulse ($V2_P$) is timed such that an evoked depolarization of the V2 is effected in fusion with the intrinsic depolarization of the first depolarizing ventricle (V1), resulting in a ventricular resynchronization. In this way, the V2 pacing pulse ($V2_P$) may pre-excite the conduction delayed V2 and help fuse the activation of the V2 with the activation of the V1 from intrinsic conduction. The interval of time between the V2 pacing pulse ($V2_P$) and the V2 sensing event ($V2_S$) of the same cardiac cycle may be referred to as the adjusted PEI.

In some examples disclosed by U.S. Patent Application Publication No. 2010/0198291 by Sambelashvili et al., the predetermined period of time at which an IMD delivers the V2 pacing pulse ($V2_P$) following an atrial pace or sense event ($A_{P/S}$) is substantially equal to the duration of time between an atrial event (sensed or paced) ($A_{P/S}$) and a V2 sensing event ($V2_S$) of at least one prior cardiac cycle decremented by a duration of time referred to as an adjusted PEI. That is, in some examples, the adjusted PEI indicates the desired interval of time between the delivery of the V2 pacing pulse ($V2_P$) and the V2 sensing event ($V2_S$) of the same cardiac cycle. One example equation that may be used to determine the timing of a fusion pacing pulse using a technique described by U.S. Patent Application Publication No. 2010/0198291 by Sambelashvili et al. is:

$$A_{P/S}-V2_P=(A_{P/S}-V2_S)-\text{adjusted PEI} \qquad \text{Equation (2):}$$

The duration of time between an atrial pace or sense event ($A_{P/S}$) and a V2 sensing event ($V2_S$) may be referred to as an atrioventricular (AV) interval or delay. The adjusted PEI may indicate an interval of time prior to a V2 sensing event ($V2_S$) at which it may be desirable to deliver the V2 pacing pulse ($V2_P$) in order to pre-excite the V2 and merge the electromechanical performance of V2 and V1 into a fusion event. In some examples described by U.S. Patent Application Publication No. 2010/0198291 by Sambelashvili et al., an adjusted PEI is a linear function that is based on V1 sensing event ($V1_S$) and a V2 sensing event ($V2_S$) of the same cardiac cycle, based on the time between an atrial pace or sense event ($A_{P/S}$) and a V2 sensing event, or any combination thereof.

As an example, adjusted PEI may be determined as follows:

$$\text{Adjusted PEI} = a(V1_S - V2_S) + b \qquad \text{Equation (3):}$$

According to U.S. Patent Application Publication No. 2010/0198291 by Sambelashvili et al., in Equation (3), the coefficients "a" and "b" may be fixed, empiric coefficients that are selected by a clinician or determined based on an adjusted PEI value selected by a clinician. In some examples, the coefficient "a" in Equation (3) may be about 1 and the coefficient "b" may be substantially equal to the PEI. In this case, the adjusted PEI is substantially equal to a time interval between a V1 sensing event ($V1_S$) and a V2 sensing event ($V2_S$) of the same cardiac cycle, incremented by the PEI. As a result, the $A_{P/S}-V2_P$ interval for timing the delivery of a V2 pacing pulse may be determined as follows $$A_{P/S} - V2_P = (A_{P/S} - V2_S) - [(V1_S - V2_S) + \text{PEI}] \qquad \text{Equation (4):}$$

Other values for the "a" and "b" coefficients in Equation (2) may be selected. In addition, other types of fusion pacing configurations may also be used in accordance with the techniques described herein. For example, other fusion pacing intervals described by U.S. Pat. No. 7,181,286 to Burnes et al. and U.S. Patent Application Publication No. 2010/0198291 by Sambelashvili et al. can also be used to control fusion pacing in accordance with techniques described herein. An example of CRT is described in U.S. Pat. No. 6,871,096 to Hill, which is entitled "SYSTEM AND METHOD FOR BI-VENTRICULAR FUSION PACING" and is incorporated herein by reference in its entirety.

In contrast to fusion pacing, in a biventricular pacing configuration, the medical device may deliver pacing pulses to both the LV and the RV in order to resynchronize the contraction of the LV and RV. In a biventricular pacing configuration, a medical device may deliver stimulation to coordinate contraction of the LV and the RV, even in the absence of intrinsic AV conduction of the heart.

In some proposed adaptive CRT pacing techniques, a pacing configuration (e.g., fusion pacing or biventricular pacing) and timing of the pacing pulses (e.g., a fusion pacing interval, such as a $A_{P/S}-V2_P$ interval, or biventricular pacing intervals, such as an $A_{P/S}-V1_P$ and $A_{P/S}-V2_P$ intervals, or an $A_{P/S}-V1_P$ and $V1_P-V2_P$ intervals) are periodically adjusted based on periodic intrinsic conduction measurements in an attempt to achieve more efficient physiologic pacing and optimal hemodynamics. For example, some proposed cardiac rhythm management medical devices are configured to deliver adaptive CRT by delivering pacing to a heart of a patient in accordance with a fusion pacing configuration and, if loss of intrinsic AV conduction is detected (e.g., AV block), switching to a biventricular pacing configuration. Thus, a medical device configured for adaptive CRT may be configured to switch from a fusion pacing configuration to a biventricular pacing configuration in response to determining a heart of a patient is no longer intrinsically conducting. Biventricular pacing may consume more energy (compared to fusion pacing) due to the delivery of pacing to both the LV and the RV, and, accordingly, delivering fusion pacing until loss of intrinsic conduction may be a more efficient use of the power stored by a power source of a medical device compared to continuously delivering biventricular pacing.

In some existing proposed techniques for delivering adaptive CRT, a medical device switches from a fusion pacing configuration to a biventricular pacing configuration if the loss of intrinsic AV conduction is detected based on a measurement of intrinsic conduction time, which may be performed as part of the fusion-pacing interval determination. For example, loss of intrinsic AV conduction may be detected if a measured A–V1 conduction time ($A_{P/S}-V1_S$) is greater than (or greater than or equal to in some examples) a predetermined threshold value. In some examples, the predetermined threshold value is selected based on previous intrinsic conduction time intervals (e.g., may be a percentage of a mean or median of a certain number of prior intrinsic conduction time measurements). In other examples, the predetermined threshold value may be selected by a clinician to be, for example, a value that indicates the depolarization time of V1 that results maintenance of cardiac output at a desirable level.

In order to measure intrinsic conduction time, the CRT pacing delivered by the medical device to the heart may be suspended to allow the heart of the patient to conduct in the absence of cardiac rhythm management therapy and to avoid interference between the delivery of pacing pulses and sensing of ventricular activation. In some examples, if pacing is delivered to an atrium of the heart, such pacing may be maintained, while pacing to the ventricles may be suspended. The measurement of intrinsic conduction time may be determined, e.g., as the time between an atrial pace or sense event ($A_{P/S}$) and a V1 sensing event ($V1_S$), which may be referred to generally as an $A-V_s$ interval. In such examples, the determinations of the intrinsic conduction time measurements may take place, for example, once a minute, once an hour, or once every 24 hours, although other frequencies may also be used.

The determinations of intrinsic conduction time may involve the suspension of some or all pacing therapy to the heart of the patient for at least one cardiac cycle, which may reduce the amount of synchronization of the ventricles of the heart during at least that one cardiac cycle. However, as described herein, the devices, systems, and techniques for providing adaptive CRT are directed to providing adaptive CRT while lessening the frequency at which the delivery of electrical stimulation to the heart of the patient is suspended.

FIG. 1 illustrates example medical device system 10 in conjunction with patient 14. Medical device system 10 is an example of a medical device system that is configured to implement the example techniques described herein for controlling the delivery of CRT to heart 12 of patient 14. In some examples, medical device system 10 includes an implantable medical device (IMD) 16 in communication with external device 24. In the illustrated example, IMD 16 may be coupled to leads 18, 20, and 22. IMD 16 may be, for example, an implantable pacemaker that provides electrical signals to heart 12 and senses electrical activity of heart 12 via electrodes coupled to one or more of leads 18, 20, and 22. In some examples, IMD 16 may include cardioversion and/or defibrillation capabilities.

Leads 18, 20, 22 extend into heart 12 of patient 14 to sense electrical activity of heart 12 and to deliver electrical stimulation to heart 12. In the example shown in FIG. 1, right ventricular (RV) lead 18 extends through one or more veins (not shown), the superior vena cava (not shown), and right atrium (RA) 26, and into RV 28. Left ventricular (LV) coronary sinus lead 20 extends through one or more veins, the vena cava, right atrium 26, and into the coronary sinus 30 to a region adjacent to the free wall of LV 32 of heart 12. Right atrial (RA) lead 22 extends through one or more veins and the vena cava, and into the RA 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 may also sense electrical signals attendant to the depolarization and repolarization of heart 12 via extravascular electrodes (e.g., electrodes positioned outside the vasculature of patient 14), such as epicardial electrodes, external surface electrodes, subcutaneous electrodes, and the like. The configurations of electrodes used by IMD 16 for sensing and pacing may be unipolar or bipolar.

IMD 16 is configured to provide adaptive CRT to heart 12. In some examples, as part of the adaptive CRT, IMD 16 is configured to deliver at least one of fusion pacing to heart 12 and biventricular pacing to heart 12. In some examples of fusion pacing, IMD 16 may deliver a pacing stimulus (e.g., a pacing pulse) to LV 32 via electrodes of lead 20, where the pacing stimulus is timed such that an evoked depolarization of LV 32 is effected in fusion with the intrinsic depolarization of RV 28, resulting in a ventricular resynchronization. In this way, the pacing pulse delivered to LV 32 ($LV_P$) may pre-excite a conduction delayed LV 32 and help fuse the activation of LV 32 with the activation of RV 28 from intrinsic conduction. The fusion of the depolarization of LV 32 and RV 28 may result in synchronous activation and contraction of LV 32 with RV 28. In the examples described herein, the fusion pacing configuration may be referred to as "left-ventricular" pacing. However, it should be understood that a fusion pacing configuration may also include right-ventricular pacing in any of the examples described.

In some examples, when IMD 16 is in a biventricular pacing configuration, IMD 16 may deliver a pacing stimulus (e.g., a pacing pulse) to RV 28 via electrodes of lead 18 and a pacing stimulus to LV 32 via electrodes of lead 20 in a manner that synchronizes activation and contraction of RV 28 and LV 28.

As discussed in further detail below, IMD 16 may be configured to adjust one or more pacing parameters based on a cardiac status of heart 12. In some examples, IMD 16 may be configured to adjust a pacing parameter by delivering electrical stimulation therapy to heart 12 according to either a fusion pacing configuration or a biventricular pacing configuration. In other examples, IMD 16 may be configured to adjust a pacing parameter by modifying an $A-V_P$ interval that controls the timing of ventricular pacing. In still other examples, IMD 16 may be configured to adjust a pacing parameter by increasing or decreasing the pacing output (e.g., the frequency of pacing pulses or the intensity of the pacing pulses, such as the current or voltage amplitude). In such examples, the cardiac status of heart 12 may include a heart rate of heart 12, and a respective anticipated value for an interval between an atrial event and a ventricular event, as determined or selected by one or more components of IMD 16.

As described in some examples herein, an interval between an atrial event and a ventricular event may be referred to as an "A-V interval." While IMD 16 may periodically measure an intrinsic $A-V_s$ interval of heart 12, such as for the purpose of updating a respective anticipated value for an A-V interval, IMD 16 may more frequently determine whether adjust one or more pacing parameters based on a heart rate of heart 12, and one or more respective anticipated values of an A-V interval of heart 12. In this way, the one or more respective values of an anticipated A-V interval for a given heart rate may allow IMD 16 to determine pacing parameters that may be appropriate for the treatment needs of patient 14 at a given time.

An anticipated value of an A-V interval is not an actual current measurement of intrinsic A-V conduction time, but rather may be an inferred based on a heart rate of heart 12 and previous measurements of $A-V_s$ conduction time. As discussed below in greater detail with respect to FIG. 6, a memory of IMD 16 may store at least one respective value for an A-V interval for each of a plurality of heart rates, e.g., in the form of a look-up table. In this example, a respective anticipated value for an A-V interval for a given heart rate may be considered an anticipated value of the intrinsic $A-V_s$ conduction time of heart 12 that is expected to occur at the given heart rate. Thus, by selecting pacing parameters based on a determined heart rate of heart 12 and one or more respective anticipated values for an A-V interval, IMD 16 may select pacing parameters, such as an $A-V_P$ interval or a pacing configuration, without necessarily suspending the delivery of CRT to determine an actual measurement of a current $A-V_s$ interval.

In some cases, it may be advantageous for IMD 16 to be configured to select pacing parameters without suspending CRT. For example, the clinical outcomes of some cardiac conditions for which CRT is indicated may be improved when biventricular pacing comprises a relatively greater proportion of the CRT delivered to heart 12 by IMD 16. However, if an anticipated value for an A-V interval is not used to select pacing parameters, it may be necessary for an IMD to suspend CRT each time that pacing parameters are to be selected or confirmed, in order to allow for the determination of an actual measurement of a current $A-V_s$ interval. In some known examples, this may be done approximately once per minute, in order to adapt the pacing configuration of a CRT system to changing cardiac rhythm characteristics. In such known examples, the suspension of some or all pacing therapy to the heart of the patient for at least one cardiac cycle, during which a current $A-V_s$ interval is measured, may reduce the extent of synchronization of RV 28 and LV 32 of heart 12 during at least that one cardiac cycle. A reduced amount of synchronization may limit the frequency at which a suspension of pacing therapy may be tolerated. Thus, examples that rely on the measurement of a current $A-V_s$ interval for the adaptation of CRT may provide less effective therapy delivery than the examples described herein.

In some examples, the adaptive CRT provided by IMD 16 may be useful for maintaining the cardiac rhythm in patient 14 with a conduction dysfunction, which may result when the natural electrical activation system of heart 12 is disrupted. The natural electrical activation system of a human heart 12 involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

In a normal electrical activation sequence, the cardiac cycle commences with the generation of a depolarization wave at the SA Node in the wall of RA 26. The depolarization wave is transmitted through the atrial conduction pathways of Bachmann's Bundle and the Internodal Tracts at the atrial level into the LA 33 septum. When the atrial depolarization wave has reached the AV node, the atrial septum, and the furthest walls of the right and left atria 26, 33, respectively, the atria 26, 33 may contract as a result of the electrical activation. The aggregate right atrial and left atrial depolarization wave appears as the P-wave of the PQRST complex of an electrical cardiac signal, such as a cardiac electrogram (EGM) or electrocardiogram (ECG). When the amplitude of the atrial depolarization wave passing between a pair of unipolar or bipolar pace/sense electrodes located on or adjacent RA 26 and/or LA 33 exceeds a threshold, it is detected as a sensed P-wave. The sensed P-wave may also be referred to as an atrial sensing event, or an RA sensing event (RAs). Similarly, a P-wave sensed in the LA 33 may be referred to as an atrial sensing event or an LA sensing event (LAs).

During or after the atrial contractions, the AV node distributes the depolarization wave inferiorly down the Bundle of His in the intraventricular septum. The depolarization wave may travel to the apical region of heart 12 and then superiorly though the Purkinje Fiber network. The aggregate right ventricular and left ventricular depolarization wave and the subsequent T-wave accompanying repolarization of the depolarized myocardium may appear as the QRST portion of the PQRST cardiac cycle complex. When the amplitude of the QRS ventricular depolarization wave passing between a bipolar or unipolar pace/sense electrode pair located on or adjacent RV 28 and/or LV 32 exceeds a threshold, it is detected as a sensed R-wave. The sensed R-wave may also be referred to as a ventricular sensing event, an RV sensing event ($RV_S$), or an LV sensing event ($LV_S$) depending upon the ventricle in which the electrodes of one or more of leads 18, 20, 22 are configured to sense in a particular case.

Some patients, such as patients with congestive heart failure or cardiomyopathies, may have left ventricular dysfunction, whereby the normal electrical activation sequence through heart 12 is compromised within LV 32. In a patient with left ventricular dysfunction, the normal electrical activation sequence through the heart of the patient becomes disrupted. For example, patients may experience an intra-atrial conduction defect, such as intra-atrial block. Intra-atrial block is a condition in which the atrial activation is delayed because of conduction delays between RA 26 to LA 33.

As another example, a patient with left ventricular dysfunction may experience an interventricular conduction defect, such as left bundle branch block (LBBB) and/or right bundle branch block (RBBB). In LBBB and RBBB, the activation signals are not conducted in a normal fashion along the right or left bundle branches respectively. Thus, in patients with bundle branch block, the activation of either RV 28 or LV 32 is delayed with respect to the other ventricle, causing asynchrony between the depolarization of the right and left ventricles. Ventricular asynchrony may be identified by a widened QRS complex due to the increased time for the activation to traverse the ventricular conduction paths. The asynchrony may result from conduction defects along the Bundle of His, the Right and Left Bundle Branches or at the more distal Purkinje Terminals. Typical intra-ventricular peak-to-peak asynchrony can range from about 80 milliseconds (ms) to about 200 ms or longer. However, in patients who are experiencing RBBB and LBBB, the QRS complex may be widened far beyond the normal range to a wider range, e.g., about 120 ms to about 250 ms or greater.

CRT delivered by IMD 16 may help alleviate heart failure conditions by restoring synchronous depolarization and contraction of one or more chambers of heart 12. In some cases, the fusion pacing of heart 12 described herein enhances stroke volume of a patient by improving the synchrony with which RV 28 and LV 32 depolarize and contract.

The duration of a cardiac cycle of heart 12, which includes the depolarization-repolarization sequence, may change depending on various physiological factors of patient 14, such as a heart rate. As heart rate of patient 14 changes, the timing of the delivery of a pacing pulse to LV 32 ($LV_P$) during fusion pacing therapy or the timing of the delivery of pacing pulses to RV 28 ($RV_P$) and LV 32 ($LV_P$) during biventricular pacing therapy may change. Accordingly, when IMD 16 is delivering fusion pacing, such as left-ventricular pacing, to heart 12, it may be useful for IMD 16 to periodically adjust a fusion pacing interval (i.e., an A–$V_P$ interval) in order to maintain the delivery of the LV 32 pacing pulse ($LV_P$) at a time that results in a fusion of the depolarization of LV 32 and RV 28. In addition, when IMD 16 is delivering biventricular pacing therapy to heart 12, IMD 16 may periodically evaluate one or more biventricular pacing intervals (i.e., A–$V_p$ intervals) in order to maintain the delivery of the LV 32 pacing pulse ($LV_P$) at a time relative to the RV 28 pacing pulse ($RV_P$) that results in a synchrony of contraction of LV 32 and RV 28. As discussed in further detail below, in some examples, IMD 16 adjusts the A–$V_p$ interval for fusion pacing or for biventricular pacing based on a determined heart rate of a cardiac cycle and a respective anticipated A–V interval, where the respective anticipated A–V interval is selected from a table stored in a memory of IMD 16 based on a heart rate of heart 12 determined by IMD 16. As such, with respect to an interval selected by processing circuitry 80 of IMD 16 (described in further detail below with respect to FIG. 3), an anticipated interval may be referred to as a "selected value of an A–V interval," or, with respect to a given heart rate, a "respective selected value of an A–V interval."

In some examples, IMD 16 delivers pacing pulses to LV 32 until IMD 16 determines that selected value for an A–V interval associated with a determined heart rate of heart 12 exceeds a threshold for fusion or left-ventricular pacing therapy. In some cases, upon determining that a selected value for an A–V interval exceeds such a threshold, IMD 16 switches to a different pacing configuration, such as a biventricular pacing configuration, after discontinuing fusion pacing therapy. Similarly, IMD 16 may deliver pacing pulses to LV 32 and RV 28 in a biventricular pacing configuration until IMD 16 determines that a respective selected value for an A–V interval associated with a determined heart rate of heart 12 does not exceed a threshold for left-ventricular pacing therapy, at which time IMD 16 may switch to a fusion pacing configuration, such as left-ventricular pacing.

In some examples, IMD 16 also provides defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical shocks. In some examples, IMD 16 is programmed to deliver a progression of therapies, e.g., shocks with increasing energy levels, until a fibrillation of heart 12 is stopped. In examples in which IMD 16 provides defibrillation therapy and/or cardioversion therapy, IMD 16 may detect fibrillation by employing any one or more fibrillation detection techniques known in the art.

In some examples, external device 24 may be a handheld computing device or a computer workstation. External device 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, or other clinician, may interact with external device 24 to communicate with IMD 16. For example, the user may interact with external device 24 to retrieve physiological or diagnostic information from IMD 16. A user may also interact with external device 24 to program IMD 16, e.g., to select values for operational parameters of the IMD.

For example, the user may use external device 24 to retrieve information from IMD 16 regarding the rhythm of heart 12, trends therein over time, or arrhythmia episodes. As another example, the user may use external device 24 to retrieve information from IMD 16 regarding other sensed physiological parameters of patient 14, such as sensed electrical activity, activity, posture, respiration, or thoracic impedance. As another example, the user may use external device 24 to retrieve information from IMD 16 regarding the performance or integrity of IMD 16 or other components of system 10, such as leads 18, 20, and 22, or a power source of IMD 16. In such examples, physiological parameters of patient 14 and data regarding IMD 16 may be stored in a memory of IMD 16 for retrieval by the user.

The user may use external device 24 to program a therapy progression, select electrodes used to deliver defibrillation pulses, select waveforms for the defibrillation pulse, or select or configure a fibrillation detection algorithm for IMD 16. The user may also use external device 24 to program aspects of other therapies provided by IMD 14, such as cardioversion or pacing therapies. In some examples, the user may activate certain features of IMD 16 by entering a single command via external device 24, such as depression of a single key or combination of keys of a keypad or a single point-and-select action with a pointing device.

IMD 16 and external device 24 may communicate via wireless communication using any techniques known in the art. Examples of communication techniques may include, for example, include radiofrequency (RF) telemetry, which may be an RF link established via an antenna according to Bluetooth, WiFi, or medical implant communication service (MICS), though other techniques are also contemplated. In some examples, external device 24 may include a programming head that may be placed proximate to the patient's body near the IMD 16 implant site in order to improve the quality or security of communication between IMD 16 and external device 24.

Figure 2:
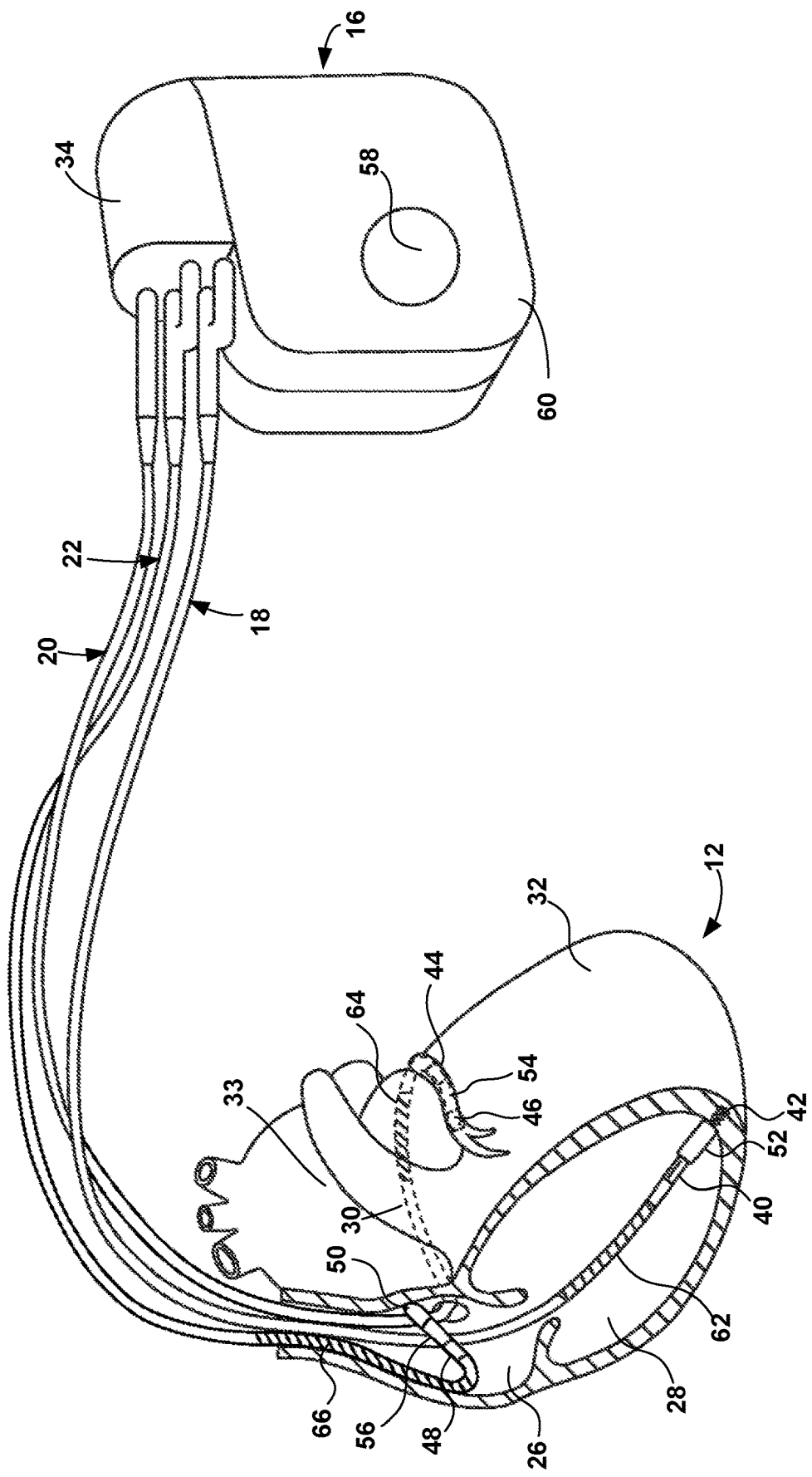
FIG. 2 is a conceptual diagram illustrating the medical device and leads of the medical device system of FIG. 1 in greater detail.

FIG. 2 is a conceptual diagram illustrating IMD 16 and leads 18, 20, 22 of medical device system 10 in greater detail. Leads 18, 20, 22 may be electrically coupled to therapy delivery circuitry, sensing circuitry, or other circuitry of IMD 16 via connector block 34. In some examples, proximal ends of leads 18, 20, 22 include electrical contacts that electrically couple to respective electrical contacts within connector block 34. In addition, in some examples, leads 18, 20, 22 are mechanically coupled to connector block 34 with the aid of set screws, connection pins or another suitable mechanical coupling mechanism.

Each of the leads 18, 20, 22 includes an elongated insulative lead body, which may carry a number of conductors separated from one another by tubular insulative sheaths. In the illustrated example, bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. Electrodes 40, 44, and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses to LV 32 via electrodes 44, 46 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48, and 50 may be used for unipolar sensing or stimulation delivery in combination with housing electrode 58. As described in further detail with reference to FIG. 3, housing 60 may enclose therapy delivery circuitry that generates cardiac pacing pulses and defibrillation or cardioversion shocks, as well as sensing circuitry for monitoring the patient's heart rhythm.

In some examples, leads 18, 20, 22 may also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is one example, and is not intended to be limiting. In other examples, a therapy system may include extravascular electrodes, such as subcutaneous electrodes, epicardial electrodes, and/or patch electrodes, instead of or in addition to the electrodes of transvenous leads 18, 20, 22 illustrated in FIG. 1. Further, IMD 16 need not be implanted within patient 14. In examples in which IMD 16 is not implanted in patient 14, IMD 16 may deliver defibrillation pulses, pacing pulses, and other therapies to heart 12 via percutaneous leads that extend through the skin of patient 14 to a variety of positions within or outside of heart 12.

Figure 3:
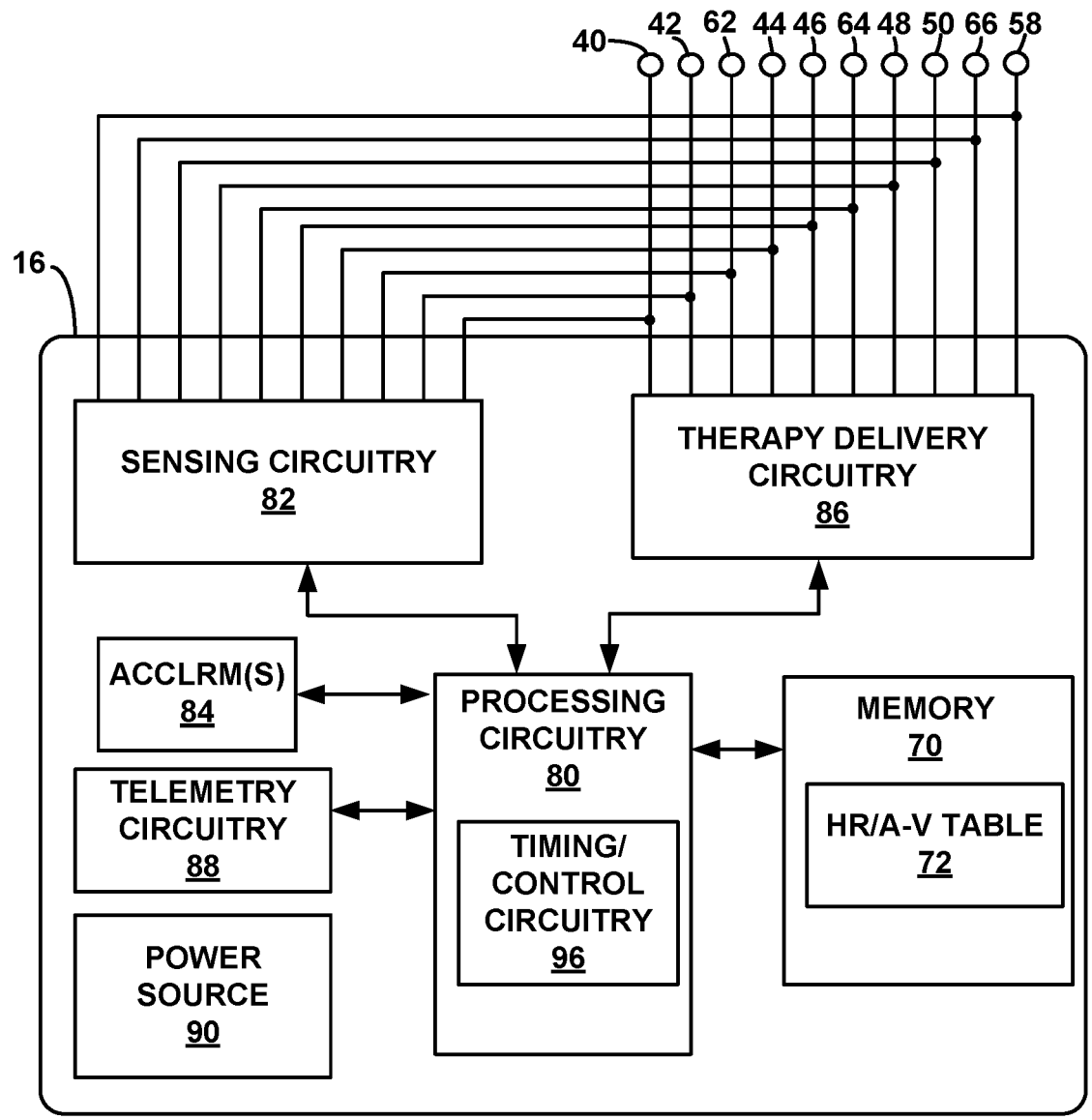
FIG. 3 is a functional block diagram of an example implantable medical device that delivers CRT to a heart of a patient.

In other examples of medical device systems that provide electrical stimulation therapy to heart 12, a therapy system may include any suitable number of leads coupled to IMD 16, and each of the leads may extend to any location within or proximate to heart 12. For example, a therapy system may include a dual chamber device rather than a three-chamber device as shown in FIG. 1. In one example of a dual chamber configuration, IMD 16 is electrically connected to a single lead that includes stimulation and sense electrodes within LV 32 as well as sense and/or stimulation electrodes within RA 26, as shown in FIG. 3. In another example of a dual chamber configuration, IMD 16 is connected to two leads that extend into a respective one of RA 28 and LV 32.

In some examples, a medical device system includes one or more intracardiac pacing devices instead of, or in addition to, an IMD coupled to leads that extend to heart 12, like IMD 16. The intracardiac pacing devices may include therapy delivery and processing circuitry within a housing configured for implantation within one of the chambers of heart 12. In such systems, the plurality of pacing devices, which may include one or more intracardiac pacing devices and/or an IMD coupled to one or more leads, may communicate to coordinate sensing and pacing in various chambers of heart 12 to provide CRT according to the techniques described herein. Processing circuitry and memory of one or more of the pacing devices, and/or another implanted or external medical device, may provide the functionality for controlling delivery of CRT ascribed to processing circuitry and memory of IMD 16 herein.

FIG. 3 is a functional block diagram of one example configuration of IMD 16 of FIGS. 1 and 2. In the illustrated example, IMD 16 includes memory 70, processing circuitry 80, sensing circuitry 82, one or more accelerometers 84, therapy delivery circuitry 86, telemetry circuitry 88, and power source 90, one or more of which may be disposed within housing 60 of IMD 16. In some examples, memory 70 includes computer-readable instructions that, when executed by processing circuitry 80, cause IMD 16 and processing circuitry 80 to perform various functions attributed to IMD 16 and processing circuitry 80 herein. Memory 70 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. In addition to sensed physiological parameters of patient 14 (e.g., EGM or ECG signals), one or more time intervals for timing fusion pacing therapy and biventricular pacing therapy to heart 12 (e.g., PEI values, adjusted PEI values, biventricular pacing intervals, or any combination thereof) may be stored by memory 70.

Figure 4:
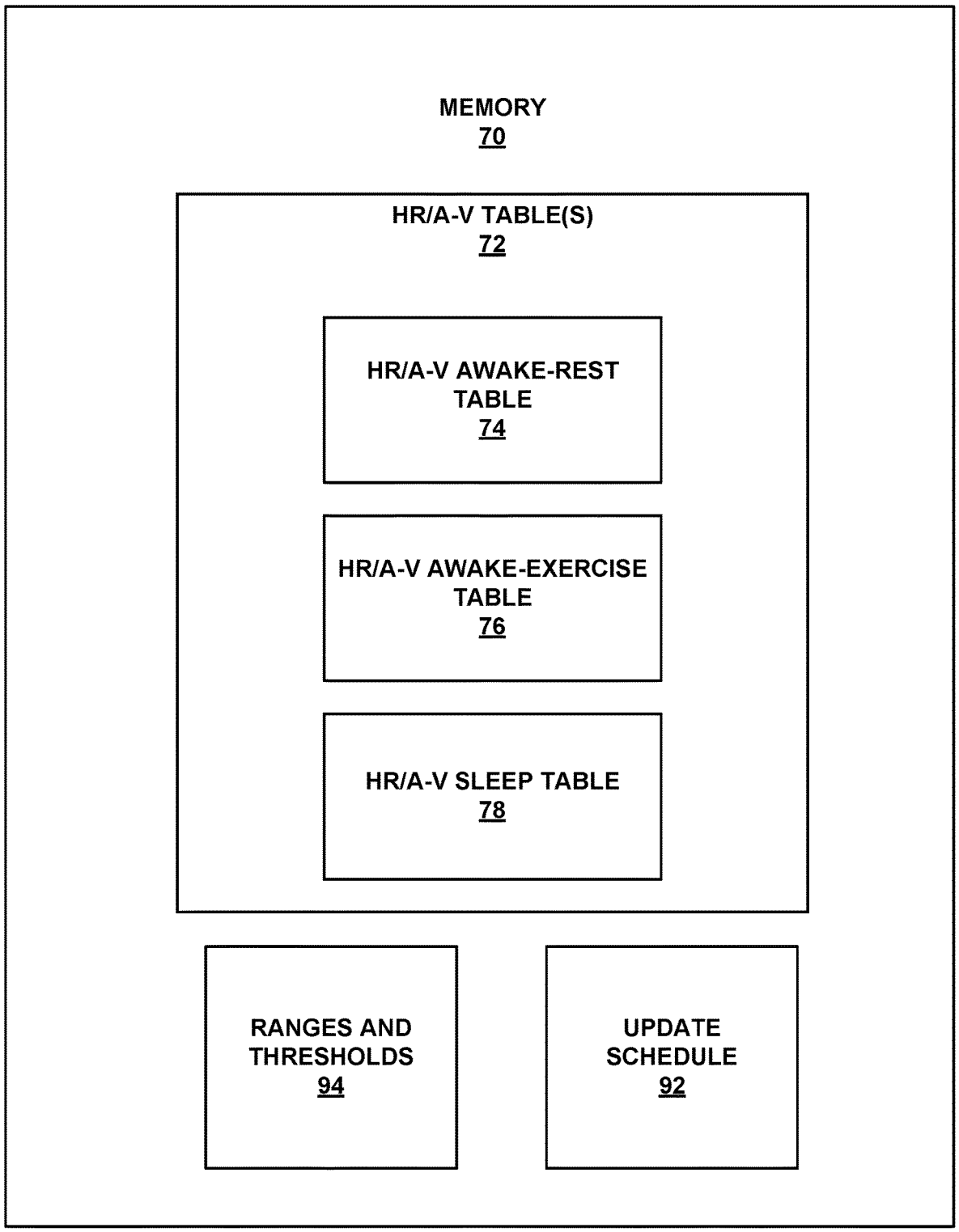
FIG. 4 is a functional block diagram of the memory of FIG. 3 in greater detail.

As illustrated in the example of FIGS. 3 and 4, memory 70 may include one or more heart rate/A–V interval tables 72. In some examples, heart rate/A–V interval tables 72 may include a plurality of heart rates and at least one respective selected value for an A–V interval for each of the plurality of heart rates. As discussed in further detail below with respect to FIG. 7, one or more of the selected values for an A–V interval stored within heart rate/A–V interval tables 72 may be updated according to update schedule 92. For example, memory 70 may include computer-readable instructions that, when executed by processing circuitry 80, cause processing circuitry 80 periodically to determine a heart rate of heart 12, suspend the delivery of CRT by therapy delivery circuitry 86, measure a current value of an A–V interval, and determine whether the measured current value for the A–V interval is not sufficiently similar to, e.g., falls outside of a range about, the respective selected value for an A–V interval stored in table 72 for the determined heart rate. If the measured current value for the A–V interval is not sufficiently similar to the respective selected value for an A–V interval associated with the heart rate, processing circuitry 80 may then update table 72, e.g., by replacing the respective selected value for the A–V interval associated with the heart rate with the current value for the A–V interval.

Processing circuitry 80 may include one or more of a microprocessor, a controller, digital signal processing circuitry (DSP), an application specific integrated circuit (ASIC), a field-programmable gate array (FPGA), or equivalent discrete or integrated logic circuitry. In some examples, processing circuitry 80 may include multiple components, such as any combination of one or more microprocessors, one or more controllers, one or more DSPs, one or more ASICs, or one or more FPGAs, as well as other discrete or integrated logic circuitry. The functions attributed to processing circuitry 80 herein may be embodied as software, firmware, hardware or any combination thereof. Processing circuitry 80 may be configured to determine a heart rate of heart 12 based on electrical activity sensed by sensing circuitry 82, select a respective A–V interval value associated with the heart rate from table 72 of memory 70, and determine whether to control therapy delivery circuitry 86 to deliver CRT to heart 12 according to a fusion pacing configuration or a biventricular pacing configuration based on the selected A–V interval value. With further respect to this example, processing circuitry 80 may be configured to cause therapy delivery circuitry 86 to deliver electrical pulses in accordance with the selected A–V interval value by using the selected A–V interval value as an A–$V_p$ interval between an atrial sensing or pacing event and the delivery of a pacing pulse, or determining the A–$V_p$ interval from the selected A–V interval, e.g., by subtracting a PEI from the selected A–V interval. In some examples, the A–V intervals stored in table 72 within memory 70 are intervals between a paced or sensed atrial event and a sensed (i.e., intrinsic) ventricular event, i.e., are A–$V_s$ intervals.

Sensing circuitry 82 is configured to monitor signals from at least one of electrodes 40, 42, 44, 46, 48, 50, 58, 62, 64 or 66 in order to monitor electrical activity of heart 12, e.g., via EGM signals. For example, sensing circuitry 82 may sense atrial events (e.g., a P-wave) with electrodes 48, 50, 66 within RA 26 or sense an LV 32 event (e.g., an R-wave) with electrodes 44, 46, 64 within LV 32. In some examples, sensing circuitry 82 includes switching circuitry to select which of the available electrodes are used to sense the electrical activity of heart 12. For example, processing circuitry 80 may select the electrodes that function as sense electrodes via the switching circuitry within sensing circuitry 82, e.g., by providing signals via a data/address bus. In some examples, sensing circuitry 82 includes one or more sensing channels, each of which may comprise an amplifier. In response to the signals from processing circuitry 80, the switching circuitry of sensing circuitry 82 may couple the outputs from the selected electrodes to one of the sensing channels.

In some examples, one channel of sensing circuitry 82 may include an R-wave amplifier that receives signals from electrodes 40 and 42, which are used for pacing and sensing in RV 28 of heart 12. Another channel may include another R-wave amplifier that receives signals from electrodes 44 and 46, which are used for pacing and sensing proximate to LV 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing circuitry 82 may include a P-wave amplifier that receives signals from electrodes 48 and 50, which are used for pacing and sensing in RA 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing circuitry 82 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing circuitry 82 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 70 as an EGM. In some examples, the storage of such EGMs in memory 70 may be under the control of a direct memory access circuit. Processing circuitry 80 may employ digital signal analysis techniques to characterize the digitized signals stored in memory 70 to detect and classify the patient's heart rhythm from the electrical signals. Processing circuitry 80 may detect and classify the heart rhythm of patient 14 by employing any of the numerous signal processing methodologies known in the art.

Signals generated by sensing circuitry 82 may include, for example: an RA-event signal, which indicates a detection of a P-wave via electrodes implanted within RA 26 (FIG. 1); an LA-event signal, which indicates a detection of a P-wave via electrodes implanted within LA 33 (FIG. 1); an RV-event signal, which indicates a detection of an R-wave via electrodes implanted within RV 28; or an LV-event signal, which indicates a detection of an R-wave via electrodes implanted within LV 32. In the example of therapy system 10 shown in FIGS. 1 and 2, IMD 16 is not connected to electrodes that are implanted within LA 33. However, in other example therapy systems, IMD 16 may be connected to electrodes that are implanted within LA 33 in order to sense electrical activity of LA 33.

In some examples, IMD 16 may include one or more additional sensors, such as accelerometers 84. In some examples, accelerometers 84 may comprise one or more three-axis accelerometers. Signals generated by accelerometers 84 may be indicative of, for example, gross body movement of patient 14, such as a patient posture or activity level. Regardless of the configuration of accelerometers 84, processing circuitry 80 may determine patient parameter values based on the signals obtained therefrom. Accelerometers 84 may produce and provide signals to processing circuitry 80 for a determination as to the posture and activity level of patient 14 at a given time. Processing circuitry 80 may then use the determined posture and activity level to further determine whether patient 14 is awake or asleep, and, if patient 14 is determined to be awake, to further determine whether patient 14 is at rest or exercising. As described below with respect to FIGS. 7-9, the wake/sleep and rest/exercise states of patient 14 determined by processing circuitry 80 may cause processing circuitry 80 to select a corresponding one of tables 72, and then to select one or more values of an A-V interval from the selected one of tables 72.

Therapy delivery circuitry 86 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Therapy delivery circuitry 86 is configured to generate and deliver electrical stimulation therapy. For example, therapy delivery circuitry 86 may deliver a pacing stimulus to LV 32 (FIG. 2) of heart 12, in accordance with the fusion pacing techniques described herein, via at least two electrodes 44, 46 (FIG. 2). As another example, therapy delivery circuitry 86 may deliver a pacing stimulus to RV 28 via at least two electrodes 40, 42 (FIG. 2) and a pacing stimulus to LV 32 via at least two electrodes 44, 46 (FIG. 2), e.g., in accordance with the biventricular pacing techniques described herein.

In some examples, therapy delivery circuitry 86 is configured to deliver cardioversion or defibrillation shocks to heart 12. The pacing stimuli, cardioversion shocks, and defibrillation shocks may be in the form of stimulation pulses. In other examples, therapy delivery circuitry 86 may deliver one or more of these types of stimulation in the form of other signals, such as sine waves, square waves, or other substantially continuous time signals.

Therapy delivery circuitry 86 may include a switching circuitry, and processing circuitry 80 may use the switching circuitry to select, e.g., via a data/address bus, which of the available electrodes are used to deliver defibrillation pulses or pacing pulses. The switching circuitry may include a switch array, switch matrix, multiplexer, or any other type of switching device suitable to selectively couple stimulation energy to selected electrodes. In other examples, processing circuitry 80 may select a subset of electrodes 40, 42, 44, 46, 48, 50, 58, 62, 64, and 66 with which stimulation is delivered to heart 12 without a switching circuitry.

Processing circuitry 80 may select one or more respective A-V interval values from HR/A-V interval table 72 of memory 70 for timing the delivering of pacing pulses to heart 12 based on one or more signals sensed by sensing circuitry 82. For example, processing circuitry 80 may determine a heart rate of heart 12 based on electrical activity of heart 12 sensed by sensing circuitry 82, and then select one or more respective selected A-V interval values from HR/A-V interval table 72 based on the determined heart rate. These intervals may include, for example, an A-V interval indicative of the intrinsic conduction from the atria to the ventricles (e.g., $A_{P/S}$–$RV_S$ interval, also referred to more generally as an A-$V_S$ interval). From such intervals, a pacing interval (e.g., an $A_{P/S}$–$RV_P$ and/or $A_{P/S}$–$LV_P$, also referred to more generally as an A-$V_P$ interval) for fusion pacing or biventricular pacing may be determined, e.g., by subtracting a PEI, or otherwise as described above.

Processing circuitry 80 includes pacer timing and control circuitry 96, which may be embodied as hardware, firmware, software, or any combination thereof. Pacer timing and control circuitry 96 may comprise a dedicated hardware circuit, such as an ASIC, separate from other processing circuitry 80 components, such as a microprocessor, or a software module executed by a component of processing circuitry 80 (e.g., a microprocessor or ASIC). Pacer timing and control circuitry 96 may help control the delivery of pacing pulses to heart 12 according to the one or more respective A-V interval values selected by processing circuitry 80 from HR/A-V interval table 72.

In examples in which IMD 16 delivers a pacing pulse according to the one or more A-V interval values selected and/or determined by processing circuitry 80, pacer timing and control circuitry 96 may include a timer for determining that a selected A-V interval has elapsed after processing circuitry 80 determines that an atrial pace or sense event ($A_{P/S}$, or more generally A) has occurred. The timer of pacing timing and control circuitry 96 may be configured to begin upon the detection of the preceding atrial pace or sense event ($A_{P/S}$) by processing circuitry 80. Upon expiration of the particular timer, processing circuitry 80 may control therapy delivery circuitry 86 to deliver a pacing stimulus, according to a fusion or biventricular pacing configuration, to heart 12. For example, pacing timing and control circuitry 96 may generate a trigger signal that triggers the output of a pacing pulse by therapy delivery circuitry 86.

In examples in which IMD 16 is configured to deliver other types of cardiac rhythm therapy in addition to fusion pacing and biventricular pacing, pacer timing and control circuitry 96 may also include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

In examples in which IMD 16 is configured to deliver other types of cardiac rhythm therapy in addition to CRT, intervals defined by pacer timing and control circuitry 96 within processing circuitry 80 may include atrial and ventricular pacing escape intervals, refractory periods during which sensed P-waves and R-waves are ineffective to restart timing of the escape intervals, and the pulse widths of the pacing pulses. As another example, pacer timing and control circuitry 96 may define a blanking period, and provide signals from sensing circuitry 82 to blank one or more channels, e.g., amplifiers, for a period during and after delivery of electrical stimulation to heart 12. The durations of these intervals may be determined by processing circuitry 80 in response to stored data in memory 70. In some examples, the pacer timing and control circuitry 96 of processing circuitry 80 may also determine the amplitude of the cardiac pacing pulses.

During certain pacing modes, escape interval counters within pacer timing/control circuitry 96 of processing circuitry 80 may be reset upon sensing of R-waves and P-waves. Therapy delivery circuitry 86 may include pacer output circuits that are coupled, e.g., selectively by switching circuitry, to any combination of electrodes 40, 42, 44, 46, 48, 50, 58, 62, or 66 appropriate for delivery of a bipolar or unipolar pacing pulse to one of the chambers of heart 12. Processing circuitry 80 may reset the escape interval counters upon the generation of pacing pulses by therapy delivery circuitry 86, and thereby control the basic timing of cardiac pacing functions, including fusion cardiac resynchronization therapy.

The value of the count present in the escape interval counters when reset by sensed R-waves and P-waves may be used by processing circuitry 80 to measure the durations of R–R intervals, P–P intervals, P–R intervals and R–P intervals, which are measurements that may be stored in memory 70. Processing circuitry 80 may use the count in the interval counters to detect a tachyarrhythmia event, such as ventricular fibrillation event or ventricular tachycardia event. Upon detecting a threshold number of tachyarrhythmia events, processing circuitry 80 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode.

In some examples, processing circuitry 80 may operate as an interrupt driven device, and is responsive to interrupts from pacer timing and control circuitry 96, where the interrupts may correspond to the occurrences of sensed P-waves and R-waves and the generation of cardiac pacing pulses. Any necessary mathematical calculations to be performed by processing circuitry 80 and any updating of the values or intervals controlled by the pacer timing and control circuitry 96 of processing circuitry 80 may take place following such interrupts. A portion of memory 70 may be configured as a plurality of recirculating buffers, capable of holding series of measured intervals, which may be analyzed by processing circuitry 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processing circuitry 80 may utilize all or a subset of the rule-based detection methods described in U.S. Pat. No. 5,545,182 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,182 to Olson et al. and U.S. Pat. No. 5,755,736 to Gillberg et al. are incorporated herein by reference in their entireties. However, other arrhythmia detection methodologies may also be employed by processing circuitry 80 in other examples.

If IMD 16 is configured to generate and deliver defibrillation shocks to heart 12, therapy delivery circuitry 86 may include a high voltage charge circuit and a high voltage output circuit. In the event that processing circuitry 80 determines that generation of a cardioversion or defibrillation shock is required, processing circuitry 80 may employ the escape interval counter to control timing of such cardioversion and defibrillation shocks, as well as associated refractory periods. In response to the detection of atrial or ventricular fibrillation or tachyarrhythmia requiring a cardioversion pulse, processing circuitry 80 may activate a cardioversion/defibrillation control circuitry (not shown), which may, like pacer timing and control circuitry 96, be a hardware component of processing circuitry 80 and/or a firmware or software module executed by one or more hardware components of processing circuitry 80. The cardioversion/defibrillation control circuitry may initiate charging of the high voltage capacitors of the high voltage charge circuit of therapy delivery circuitry 86 under control of a high voltage charging control line.

Processing circuitry 80 may monitor the voltage on the high voltage capacitor, e.g., via a voltage charging and potential (VCAP) line. In response to the voltage on the high voltage capacitor reaching a predetermined value set by processing circuitry 80, processing circuitry 80 may generate a logic signal that terminates charging. Thereafter, timing of the delivery of the defibrillation or cardioversion pulse by therapy delivery circuitry 86 is controlled by a cardioversion/defibrillation control circuitry (not shown) of processing circuitry 80. Following delivery of the fibrillation or tachycardia therapy, processing circuitry 80 may return therapy delivery circuitry 86 to a cardiac pacing function and await the next successive interrupt due to pacing or the occurrence of a sensed atrial or ventricular depolarization.

Therapy delivery circuitry 86 may deliver cardioversion or defibrillation shock with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching circuitry of therapy delivery circuitry 86.

Telemetry circuitry 88 includes any suitable hardware, firmware, software or any combination thereof for communicating with another device, such as external device 24 (FIG. 1). Under the control of processing circuitry 80, telemetry circuitry 88 may receive downlink telemetry from and send uplink telemetry to external device 24 with the aid of an antenna, which may be internal and/or external. Processing circuitry 80 may provide the data to be uplinked to external device 24 and the control signals for the telemetry circuit within telemetry circuitry 88, e.g., via an address/data bus. In some examples, telemetry circuitry 88 may provide received data to processing circuitry 80 via a multiplexer.

In some examples, processing circuitry 80 may transmit atrial and ventricular heart signals (e.g., EGM signals) produced by atrial and ventricular sense amp circuits within sensing circuitry 82 to external device 24. Other types of information may also be transmitted to external device 24, such as the various intervals and delays used to deliver CRT. External device 24 may interrogate IMD 16 to receive the heart signals. Processing circuitry 80 may store heart signals within memory 70, and retrieve stored heart signals from memory 70. Processing circuitry 80 may also generate and store marker codes indicative of different cardiac episodes that sensing circuitry 82 detects, and transmit the marker codes to external device 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Telemetry circuitry 88 includes any suitable hardware, firmware, software or any combination thereof for communicating with another device, such as external device 24 (FIG. 1). Under the control of processing circuitry 80, telemetry circuitry 88 may receive downlink telemetry from and send uplink telemetry to external device 24 with the aid of an antenna, which may be internal and/or external. Processing circuitry 80 may provide the data to be uplinked to external device 24 and the control signals for the telemetry circuit within telemetry circuitry 88, e.g., via an address/data bus. In some examples, telemetry circuitry 88 may provide received data to processing circuitry 80 via a multiplexer.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

FIG. 4 is a functional block diagram of memory 70 shown in greater detail. As illustrated in FIG. 4, HR/A–V table 72 may further include an HR/A–V awake-rest table 74, HR/A–V awake-exercise table 76, and HR/A–V sleep table 78. As described above with respect to FIG. 3, signals generated by accelerometers 84 may be indicative of a posture or activity level of patient 14. Processing circuitry 80 may then use the determined posture and activity level to further determine whether patient 14 is awake or asleep, and, if patient 14 is determined to be awake, to further determine whether patient 14 is at rest or exercising. In some examples, processing circuitry 80 may select a stored value for an A–V interval associated with a heart rate from one of tables 74, 76, or 78 based on the determined wake/sleep and rest/exercise states of patient 14. For example, if processing circuitry 80 determines that patient 14 is awake and in a rest state, then processing circuitry 80 may select an A–V interval value stored in HR/A–V awake-rest table 74 upon determining a heart rate of heart 12. Similarly, if processing circuitry 80 determines that patient 14 is awake and in an exercise state, then processing circuitry 80 may select an A–V interval value stored in HR/A–V awake-exercise table 76 upon determining a heart rate of heart 12. If processing circuitry determines that patient 14 is in a sleep state, then processing circuitry 80 may select an A–V interval value stored in HR/A–V sleep table 78 upon determining a heart rate of heart 12.

In some examples, the heart rates stored in tables 74, 76, and 78 may overlap to some extent. That is, the same value for a heart rate may be stored in more than one of tables 74, 76, and 78. However, even if a given heart rate is represented in more than one of tables 74, 76, and 78, the respective A–V interval values for the given heart rate may differ between tables 74, 76, and 78. For example, a heart rate of 70 bpm may be present in both table 74 and table 78, but the respective A–V interval values for the heart rate of 70 bpm may differ from table 74 to 78. This feature may reflect differences in intrinsic A–V conduction that may occur between the waking and sleeping states, even at the same heart rate. Thus, 1 MB 16 may be configured to adapt the delivery of CRT to patient 14 based on wake/sleep states and rest/exercise states, in addition to adapting the delivery of CRT based on a heart rate of patient 14.

Although not illustrated in FIG. 4, each of the one or more HR/A–V tables 72 may include two A–V interval values in association with each heart rate value. With respect to the A–V intervals described herein, atrial sensing events ($A_s$) and atrial pacing events ($A_p$) collectively may be referred to as atrial events (A). Thus, A–V interval designated as "$A$–$V_p$" may be understood as being either an $A_s$–V interval or an $A_p$–V interval. Similarly, ventricular sensing events ($V_s$) and ventricular pacing events ($V_p$) collectively may be referred to as ventricular events (V). In some examples, the first A–V interval value may be an $A_s$–V interval value indicating the time between a sensed or intrinsic atrial event and a ventricular event. The second A–V interval value may be an $A_p$–V interval value indicating the time between a paced atrial event and a ventricular event. Processing circuitry 80 may select between these two values for a determined heart rate based on whether the atrial event for a given cardiac cycle was intrinsic or paced.

As illustrated in FIG. 4, memory 70 of IMD 16 may further include update schedule 92. One or more of the A–V interval values stored within tables 72 may be updated according to update schedule 92. For example, as described above, memory 70 may include computer-readable instructions that, when executed by processing circuitry 80, cause processing circuitry 80 periodically to determine a heart rate of heart 12, suspend the delivery of CRT by therapy delivery circuitry 86, measure a current value of an A–V interval, and determine whether the measured current value for the A–V interval is sufficiently similar to a selected value for the A–V interval associated with the determined heart rate that is stored in one of tables 72. If the measured current value for the A-V interval is not sufficiently similar to the A-V interval value associated with the heart rate in the table 72, processing circuitry may update the table, e.g., by replacing the selected A-V interval value stored in the table in association with the heart rate with the currently measured value for the A-V interval.

In some examples, update schedule 92 may include computer-readable instructions for processing circuitry 80 to conduct the update technique described above according to a predetermined period. For example, update schedule 92 may direct processing circuitry 80 to update the one or more respective selected values for an A-V interval associated with a determined heart rate approximately once per hour, although other periods for periodic updates such as every several minutes every six hours, or daily, are contemplated. In this example, one or more respective selected values for an A-V interval associated with the current heart rate of heart 12, within the appropriate one of tables 72, may be determined by processing circuitry 80 at the time the update technique is conducted. For example, if processing circuitry 80 determines that patient 14 is awake and in a rest state at the time of update, then any update made to one or more selected values for an A-V interval associated with the heart rate of heart 12 at the time of update may be made to HR/A-V awake-rest table 74.

In some examples, memory 70 of IMD 16 further includes ranges and thresholds 94, as shown in FIG. 4. As discussed below with respect to FIGS. 7-9, ranges and thresholds 94 may include values that indicate a threshold degree of similarity between currently-measured and stored A-V interval values for determining whether to update the stored value. The value may be expressed as a range about one of the values, and the determination may be whether the other value is within or outside of the range. The range may be defined by an absolute difference, or percentage difference, between the values. During the execution of an update procedure according to update schedule 92, processing circuitry 80 may compare a currently measured value of an A-V interval to the selected value of the A-V interval stored in a corresponding one of tables 72 in order to determine whether to update the selected A-V interval value based on the one or more values stored as ranges and thresholds 94 in memory 70.

In addition, ranges and thresholds 94 may include threshold values for the A-V intervals stored in tables 72. During the execution of a technique to control the delivery of CRT to heart 12, processing circuitry 80 may select an A-V interval value from one of tables 72, and compare the selected A-V interval value to a threshold value 94. Depending on whether the selected A-V interval value is greater or less than the threshold value, processing circuitry 80 may determine whether to control therapy delivery circuitry 86 to deliver fusion pacing or biventricular pacing.

Figure 5:
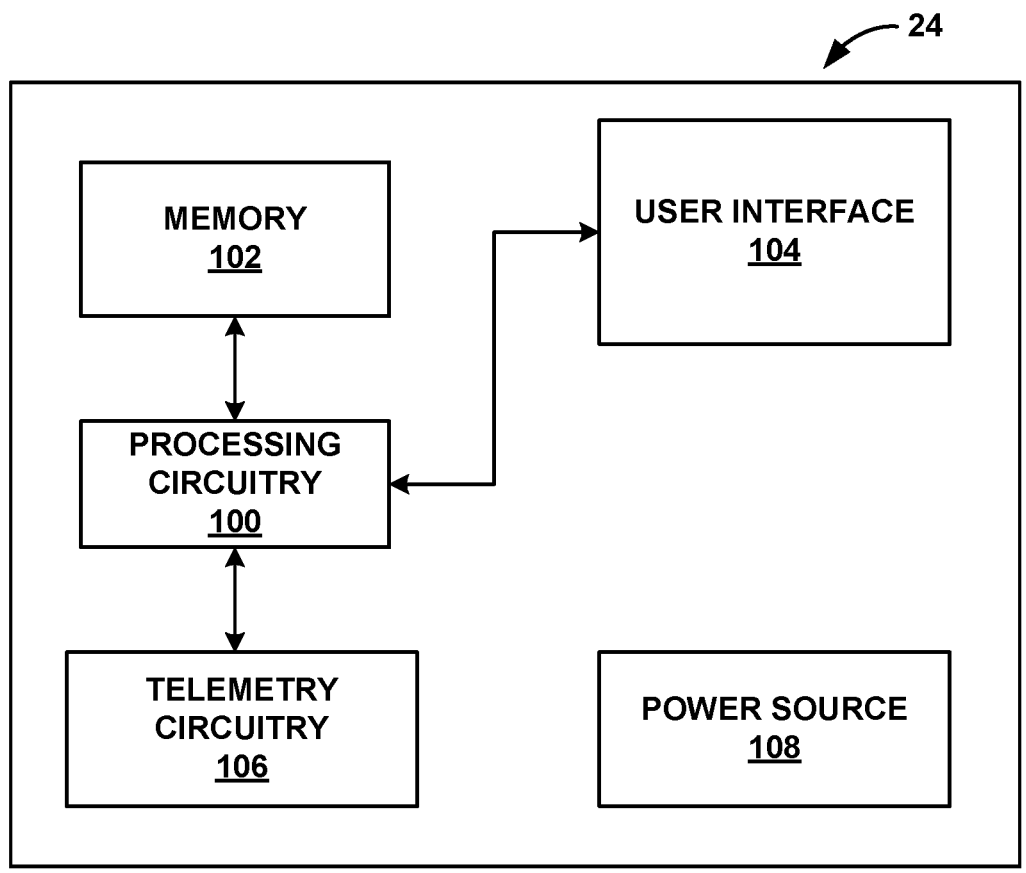
FIG. 5 is a functional block diagram of an example external medical device.

FIG. 5 is functional block diagram of an example external device 24. As shown in FIG. 5, external device 24 includes processing circuitry 100, a memory 102, a user interface 104, telemetry circuitry 106, and a power source 108. External device 24 may be a dedicated hardware device with dedicated software for interacting with IMD 16. Alternatively, external device 24 may be an off-the-shelf computing device running an application that enables external device 24 to interact with IMD 16.

A user may use external device 24 to select programmable parameters that control the monitoring and delivery of therapy by IMD 16, and to retrieve information collected by IMD regarding the condition of patient 14 or the performance of IMD 16. For example, the user may program a period for update schedule 92, values for ranges and thresholds 94, PEI values or other values for determining $A-V_p$ intervals, or any other programmable values described herein. The user may interact with external device 24 via user interface 104, which may include display to present graphical user interface to a user, and a keypad or another mechanism for receiving input from a user.

Processing circuitry 100 can take the form one or more microprocessors, DSPs, ASICs, FPGAs, programmable logic circuitry, or the like, and the functions attributed to processing circuitry 102 herein may be embodied as hardware, firmware, software or any combination thereof. Memory 102 may store instructions that cause processing circuitry 100 to provide the functionality ascribed to external device 24 herein, and information used by processing circuitry 100 to provide the functionality ascribed to external device 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before external device 24 is used to program therapy for another patient. Memory 102 may also store information that controls therapy delivery by IMD 16, such as stimulation parameter values.

External device 24 may communicate wirelessly with IMD 16, such as using RF communication or proximal inductive interaction. This wireless communication is possible through the use of telemetry circuitry 106, which may be coupled to an internal antenna or an external antenna. An external antenna that is coupled to external device 24 may correspond to the programming head that may be placed over heart 12, as described above with reference to FIG. 1.

Telemetry circuitry 106 may be similar to telemetry circuitry 88 of IMD 16 (FIG. 3). Telemetry circuitry 106 may also be configured to communicate with another computing device via wireless communication techniques, or direct communication through a wired connection. Examples of local wireless communication techniques that may be employed to facilitate communication between external device 24 and another computing device include RF communication according to the 802.11 or Bluetooth specification sets, infrared communication, e.g., according to the IrDA standard, or other standard or proprietary telemetry protocols. In this manner, other external devices may be capable of communicating with external device 24 without needing to establish a secure wireless connection.

Power source 108 is configured to deliver operating power to the components of external device 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within external device 24. In other embodiments, traditional batteries (e.g., nickel cadmium or lithium ion batteries) may be used. In addition, external device 24 may be directly coupled to an alternating current outlet to power external device 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

In some examples, processing circuitry 100 and memory 102 of external device 24 may be configured to provide some or all of the functionality ascribed to processing circuitry 80 and memory 70 of IMD 16. For example, memory 102 may be configured to store one or of HR/A-V interval tables 72, update schedule 92, or ranges and thresholds 94. In some examples, processing circuitry 100 may be configured to determine heart rates, select A-V intervals, and/or control delivery of CRT by IMD 16 as described herein with respect to processing circuitry 80 of IMD 16.

Figure 6:
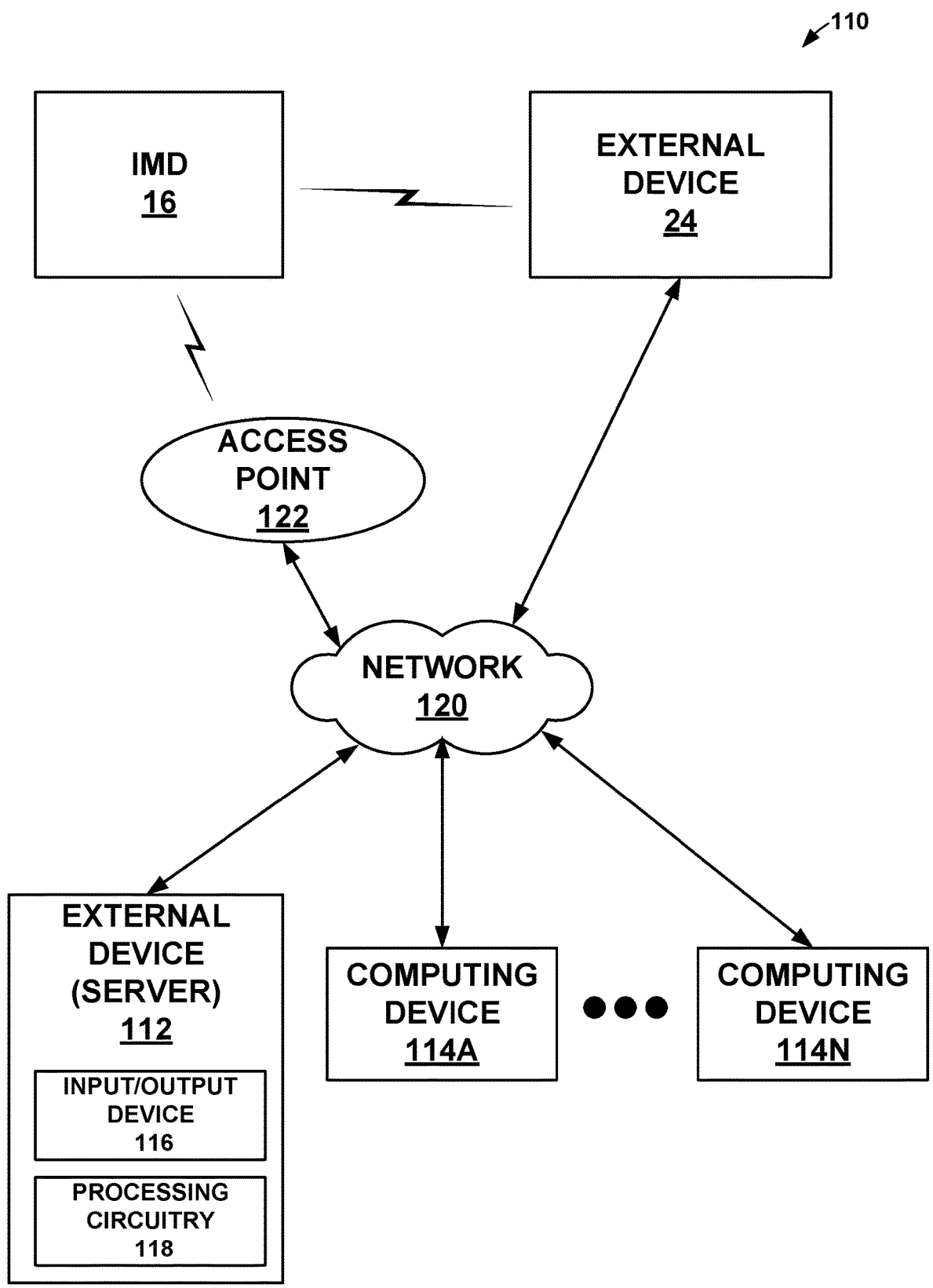
FIG. 6 is a block diagram illustrating an example system that includes an external device, such as a server, and one or more computing devices that are coupled to the IMD and external device shown in FIG. 1 via a network.

FIG. 6 is a block diagram illustrating a system 110 that includes an external device 112, such as a server, and one or more computing devices 114A-114N that are coupled to IMD 16 and external device 24 shown in FIG. 1 via a network 120, according to one example. In this example, IMD 16 uses telemetry circuitry 88 (FIG. 3) to communicate with external device 24 via a first wireless connection, and to communicate with an access point 122 via a second wireless connection. In the example of FIG. 6, access point 122, external device 24, external device 112, and computing devices 114A-114N are interconnected, and able to communicate with each other, through network 120. In some cases, one or more of access point 122, external device 24, external device 112, and computing devices 114A-114N may be coupled to network 120 through one or more wireless connections. IMD 16, external device 24, external device 112, and computing devices 114A-114N may each comprise one or more processing circuitries, such as one or more microprocessors, DSPs, ASICs, FPGAs, programmable logic circuitry, or the like, that may perform various functions and operations, such as those described herein.

Access point 122 may comprise a device that connects to network 120 via any of a variety of connections, such as telephone dial-up, digital subscriber line (DSL), or cable modem connections. In other examples, access point 122 may be coupled to network 120 through different forms of connections, including wired or wireless connections. In some examples, access point 122 may communicate with external device 24 and/or IMD 16. Access point 122 may be co-located with patient 14 (e.g., within the same room or within the same site as patient 14) or may be remotely located from patient 14. For example, access point 122 may be a home monitor that is located in the patient's home or is portable for carrying with patient 14.

During operation, IMD 16 may collect, measure, and store various forms of diagnostic data. For example, as described previously, IMD 16 may collect ECG and/or EGM signals, and determine different CRT configurations and A-V intervals. In certain cases, IMD 16 may directly analyze collected diagnostic data and generate any corresponding reports or alerts. In some cases, however, IMD 16 may send diagnostic data to external device 24, access point 122, and/or external device 112, either wirelessly or via access point 122 and network 110, for remote processing and analysis.

For example, IMD 16 may send external device 24 data that indicates whether a loss of intrinsic AV conduction was detected. External device 24 may generate reports or alerts after analyzing the data. As another example, IMD 16 may send a system integrity indication generated by processing circuitry 80 (FIG. 3) to external device 24, which may take further steps to determine whether there may be a possible condition with one or more of leads 18, 20, and 22. For example, external device 24 may initiate lead impedance tests or IMD 16 may provide lead impedance information, if such information is already available.

In another example, IMD 16 may provide external device 112 with collected EGM data, system integrity indications, and any other relevant physiological or system data via access point 122 and network 120. External device 112 includes one or more processing circuitries 118. In some cases, external device 112 may request such data, and in some cases, IMD 16 may automatically or periodically provide such data to external device 112. Upon receipt of the diagnostic data via input/output device 116, external device 112 is capable of analyzing the data and generating reports or alerts upon determination that there may be a possible condition with one or more of leads 18, 20, and 22 or with patient 14.

In one example, external device 112 may comprise a secure storage site for information that has been collected from IMD 16 and/or external device 24. In this example, network 120 may comprise an Internet network; and trained professionals, such as clinicians, may use computing devices 114A-114N to securely access stored data on external device 112. For example, the trained professionals may need to enter usernames and passwords to access the stored information on external device 112. In one embodiment, external device 112 may be a CareLink server provided by Medtronic, Inc., of Minneapolis, Minn.

In some examples, processing circuitry and memory of one or more of access point 122, server 112, or computing devices 114, e.g., processing circuitry 118 and memory of server 112, may be configured to provide some or all of the functionality ascribed to processing circuitry 80 and memory 70 of IMD 16. For example, server 112 may be configured to store one or more of HR/A-V interval tables 72, update schedule 92, or ranges and thresholds 94. In some examples, processing circuitry 118 may be configured to determine heart rates, select A-V intervals, and/or control delivery of CRT by IMD 16 as described herein with respect to processing circuitry 80 of IMD 16.

Figure 7:
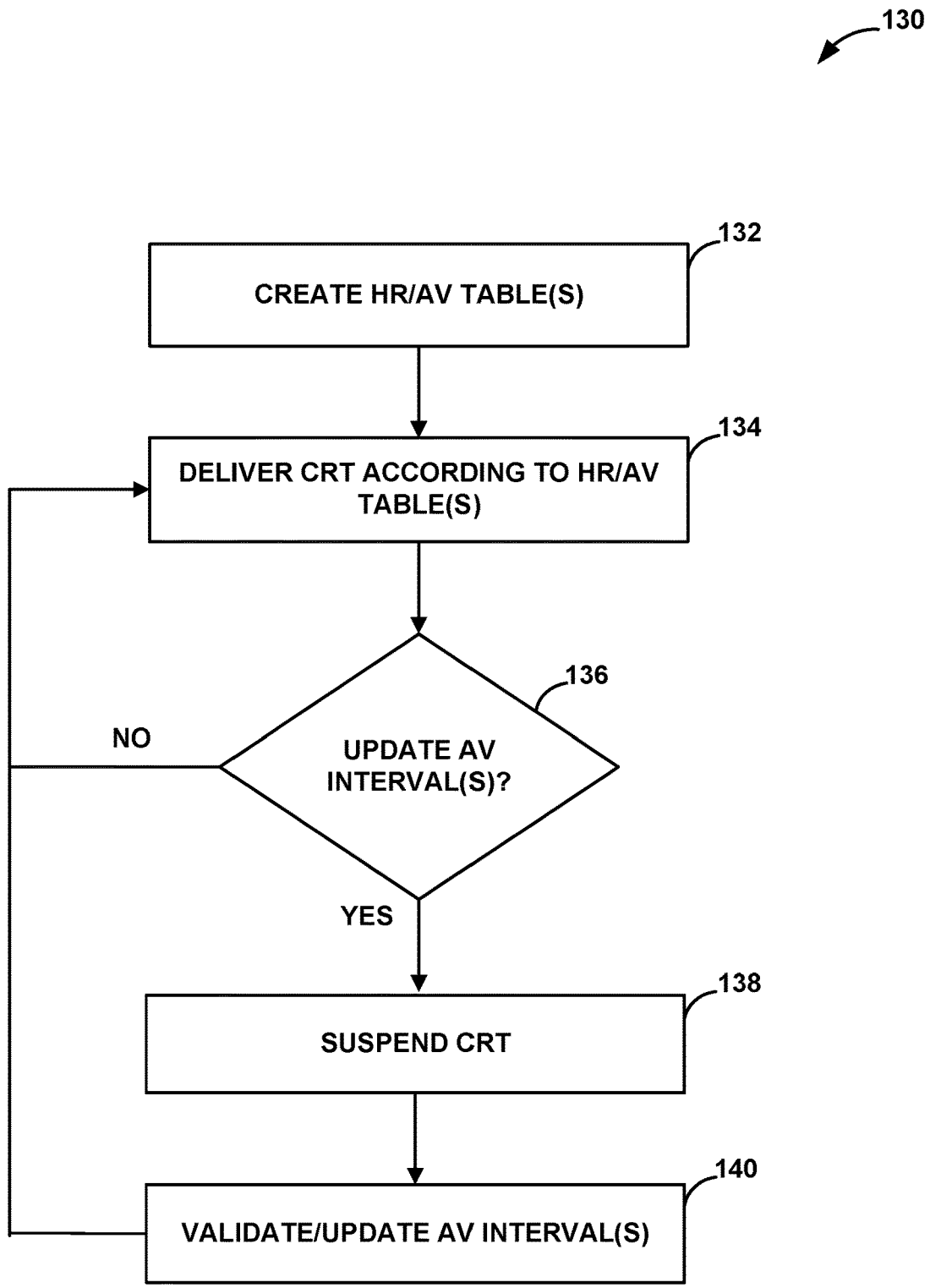
FIG. 7 is a flow diagram illustrating an example technique for creating a table of a plurality of heart rates and respective A-V intervals, delivering CRT according to the table, and updating one or more A-V interval values within the heart rate/A-V interval table.
Figure 8:
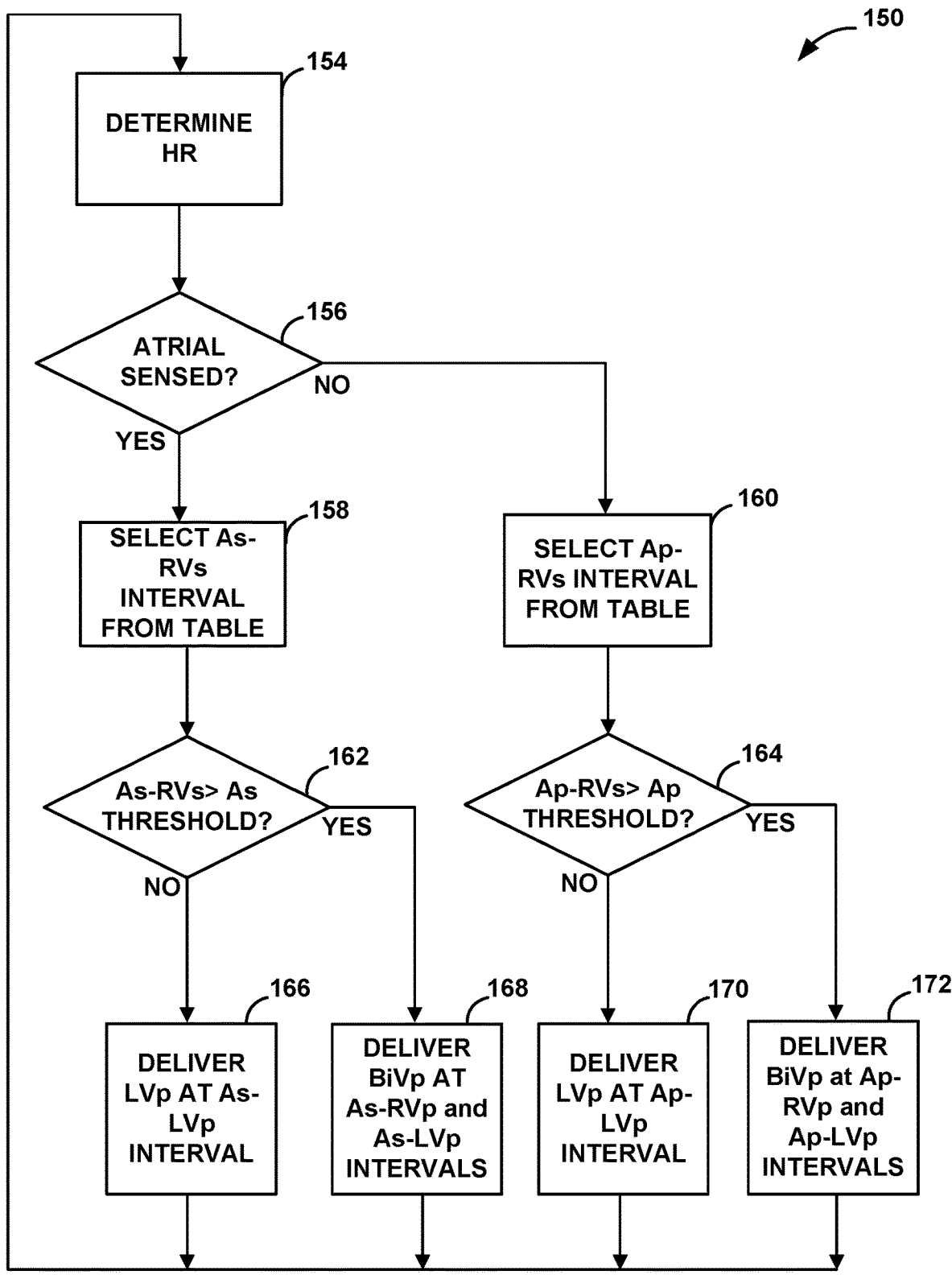
FIG. 8 is a flow diagram illustrating an example technique for delivering CRT according to one or more heart rate/A-V interval tables.
Figure 9:
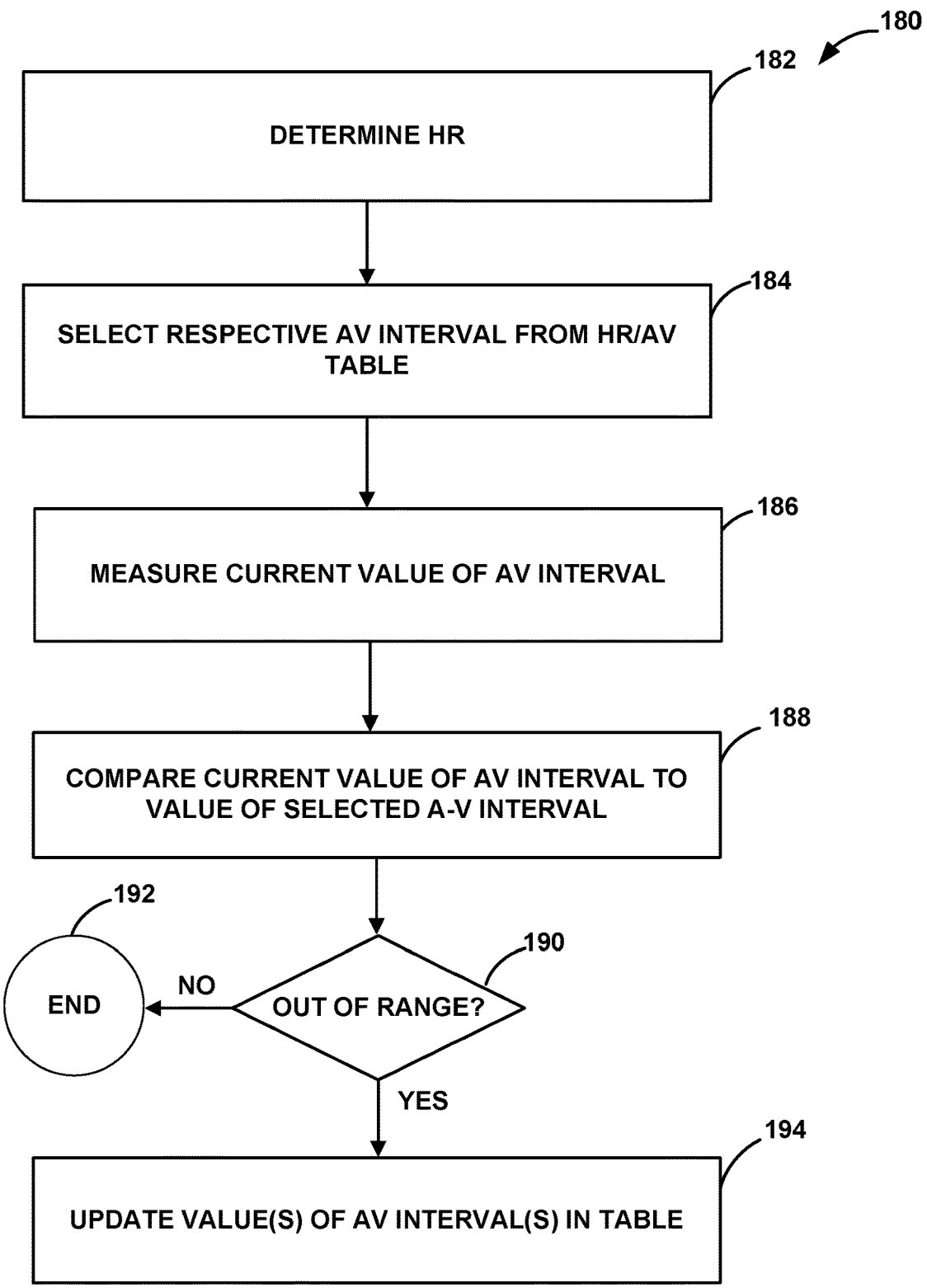
FIG. 9 is a flow diagram illustrating an example technique for updating one or more A-V interval values within a heart rate/A-V interval table.

FIGS. 7-9 are flow diagrams illustrating various techniques related to controlling delivery of adaptive CRT based on heart rate as a surrogate for more frequent measurements of intrinsic conduction in accordance with examples of this disclosure. As described herein, the techniques illustrated FIGS. 7-9 may be employed using one or more components of system 10, which have been described above with respect to FIGS. 1-6. Although described as being performed by IMD 16, the techniques of FIGS. 7-10 may be performed, in whole or in part, by processing circuitry and memory of other devices of a medical device system, as described herein.

FIG. 7 is a flow diagram illustrating an example technique 130 for creating a table (or other data structure) associating a plurality of heart rates and respective values of A-V intervals, delivering therapy according to one or more HR/A-V interval tables 72, and updating a value of a selected interval within an HR/A-V interval table 72. According to the example of FIG. 7, IMD 16 may create one or more HR/A-V interval tables (132). In some examples, IMD 16 may create the HR/A-V interval tables 72 as part of a start-up phase of treatment following the implantation of IMD 16 within patient 14.

In such examples, IMD 16 may deliver fusion pacing or biventricular pacing while processing circuitry 80 identifies a plurality of heart rates of heart 12 and determines one or more respective A-V interval values for each heart rate. For example, when processing circuitry 80 identifies a previously-unidentified heart rate of heart 12 during the start-up phase of treatment, processing circuitry 80 may then suspend CRT and measure a current A-V interval value associated with the determined heart rate. The measured A-V interval value may then be stored in one or more of tables 72, as a respective value for an A-V interval associated with the identified heart rate.

In some examples, more than one respective value for an A-V interval may be stored for the determined heart rate, such as a first A-V interval value and a second A-V interval value for that heart rate. In such examples, the first A-V interval value for a given heart rate may be an interval between a sensed or intrinsic atrial event and a ventricular event, whereas the second A-V interval value for the given heart rate may be an interval between a paced atrial event and a ventricular event. In some examples, processing circuitry 80 may expedite population of the A-V values in tables 72 by controlling therapy delivery circuitry 86 to pace the atria at various rates, and/or expedite the population of A-V interval values in tables 72 by instructing patient 14 to undertake different activities.

This process may be repeated when processing circuitry 80 identifies another heart rate of heart 12, and/or determines that patient 14 is in a different wake/sleep or rest/exercise state. In some examples, processing circuitry 80 may collect heart rates at 5-10 beat per minute (bpm) increments, and measure one or more respective A-V interval values for each 5-10 bpm increment, although other increments may be used. Although expressed in terms of bpm, the term "heart rate" as used herein encompasses any measure of the rate of depolarization or contraction of the heart, including electrical or mechanical cardiac cycle lengths, such as R-R or P-P intervals.

After the tables 72 are wholly or partially populated, control of CRT based on heart rate as a surrogate for A-V conduction delay may begin. For example, processing circuitry 80 of IMD 16 may determine a heart rate of heart 12, and control therapy delivery circuitry 86 to deliver CRT according to a stored A-V interval value associated with the determined heart rate in one of tables 72 (134), as will be described in greater detail with respect to FIG. 8.

At (136) of FIG. 7, processing circuitry 80 of IMD 16 may determine whether to update one or more of the A-V interval values stored in tables 72 of memory 70. As described above with respect to FIG. 4, update schedule 92 of memory 70 may include computer-readable instructions for processing circuitry 80 to conduct the update technique described above according to a predetermined periodic schedule. For example, update schedule 92 may direct processing circuitry 80 to validate or update one or more respective selected values for an A-V interval associated with a determined heart rate approximately once per hour. In some examples, an A-V interval value associated with the heart rate of heart 12, within the appropriate one of tables 72 as determined by processing circuitry 80 based on the activity of patient 12 at the time the update technique is conducted, may be updated. For example, if processing circuitry 80 determines that patient 14 is awake and in a rest state at the time of update, then any update made to one or more values for an A-V interval associated with the heart rate of heart 12 at the time of update will be made to HR/A-V awake-rest table 74.

If processing circuitry 80 determines that one or more values for an A-V interval are to be updated according to update schedule 92, then technique 130 may proceed to (138). If, however, processing circuitry 80 determines not to update one or more values for an AV interval, then technique 130 may proceed back to (134). At (138), processing circuitry 80 may suspend the delivery of CRT to heart 12, and perform the validation/update techniques, e.g., as described in greater detail with respect to FIG. 9 (140).

FIG. 8 is a flow diagram illustrating an example technique 150 for providing CRT according to a heart rate as a surrogate for the current A-V conduction delay, e.g., as represented by a current or recently measured A-$V_s$ interval. The example technique 150 of FIG. 8 may be performed, but is not necessarily performed, on a beat-to-beat, or per-cardiac cycle, basis. At (154), processing circuitry 80 of IMD 16 determines a heart rate of heart 12, as described above with respect to FIGS. 3 and 7. The heart rate may be a cardiac cycle length, as described above. Further, the heart rate may be a heart rate for one or more preceding cardiac cycles, such as the heart rate for the immediately preceding cardiac cycle, or a mean or median of heart rates of a plurality of preceding cycles.

Processing circuitry 80 further determines whether an atrial event for a current cardiac cycle of heart 12 was a sensed (or intrinsic) event or a paced event (156). If the atrial event for the current cardiac cycle was a sensed event (YES of 156), processing circuitry 80 selects an $A_s$-V, e.g., $A_s$-$RV_s$, value that corresponds with the determined heart rate from one of tables 72 (158). If the atrial event for the current cardiac cycle was a paced event (NO of 156), processing circuitry 80 selects an $A_p$-V, e.g., $A_p$-$RV_s$, value that corresponds with the determined heart rate from one of tables 72 (160). As discussed above with respect to FIG. 7, more than one respective value for an A-V interval may be stored in HR/A-V tables 74, 76, and 78, such that a first A-V interval value for a given heart rate may be an interval between a sensed or intrinsic atrial event and a ventricular event, whereas a second A-V interval value for the given heart rate may be an interval between a paced atrial event and a ventricular event.

According to the example of FIG. 8, processing circuitry 80 compares the selected A-$RV_s$ interval value to a threshold, which may be different depending on whether the atrial event was sensed or paced and, consequently, whether the interval is an $A_s$-V or $A_p$-V interval (162, 164). If the selected A-$V_s$ interval value is not greater than the predetermined threshold value, then processing circuitry 80 proceeds to control therapy delivery circuitry 86 to deliver fusion, e.g., left-ventricular, pacing (166, 170). If, however, the selected A-$V_s$ interval value is greater than the predetermined threshold value, then processing circuitry 80 proceeds to control therapy delivery circuitry 86 to deliver biventricular pacing (168, 172).

Processing circuitry 80 may determine the A-$V_p$ interval(s) at which to deliver the fusion or biventricular pacing based on the selected A-$V_s$ interval, e.g., based on the application of a PEI to the A-$V_s$ interval. For example, processing circuitry 80 may determine an A-$LV_p$ interval for delivery of left-ventricular fusion pacing based on the selected A-$RV_s$ interval. Processing circuitry 80 may determine an A-$RV_p$ and A-$LV_p$ interval based on the A-$RV_s$ interval, or determine one of the A-$RV_p$ and A-$LV_p$ intervals based on the A-$RV_s$ interval, and the other of the A-$RV_p$ and A-$LV_p$ intervals based on the determined interval and a programmed $RV_p$-$LV_p$ delay.

With further respect to technique 150 of FIG. 8, once processing circuitry 80 has controlled therapy delivery circuitry 86 to control therapy delivery according to one of steps (166), (168), (170), or (172), then technique 150 proceeds back to (154), at which a new heart rate of heart 12 is determined by processing circuitry 80.

FIG. 9 is a flow diagram illustrating an example technique 180 for periodically validating or updating a value of a selected A-V interval within one of HR/A-V interval tables 72. The example technique 180 of FIG. 9 may be performed periodically, with the period being greater than a cardiac cycle, such as hourly. According to the example technique 180, processing circuitry 80 determines a heart rate of heart 12, and selects a respective A-V interval value from one of HR/A-V tables 72, as described above (182).

In order to validate or update a value of a selected AV interval value in one of HR/A-V tables 72, processor 80 may suspend the delivery of CRT by IMD 16 to heart 12 (138 of FIG. 7), in order to allow heart 12 to conduct in the absence of cardiac rhythm management therapy. As discussed above, suspending the delivery of CRT may refer to, as examples, withholding ventricular pacing for one or more cardiac cycles, increasing an $A-V_p$ delay sufficiently so that intrinsic ventricular conduction may be observed, or pacing one ventricle at a sufficiently long $A-V_p$ delay and measuring intrinsic conduction on the other ventricle. While the delivery of CRT is suspended, processing circuitry 80 may measure a current value of an A-V interval without interference between the delivery of pacing pulses and sensing of ventricular activation (186). The measurement a current value of an A-V interval may represent, e.g., the time between an atrial pace or sense event ($A_{P/S}$) and a V1 sensing event ($V1_S$). In some examples, processing circuitry 80 may suspend CRT and determine a measured current value of an A-V interval, for example, approximately once per hour, although other frequencies also may be used.

Processing circuitry 80 compares the measured current value of the A-V interval of heart 12 to a value of the A-V interval stored in one or more of tables 72 that was selected based on the heart rate (188). At (190), if the measured current value of the A-V interval is within the predetermined range 94 of the selected AV interval value, then the stored A-V interval value is validated and technique 180 terminates (192).

If, however, the measured current value of the A-V interval is determined not to be within the predetermined range 94 of the selected A-V interval value (YES of 190), then processing circuitry 80 may update the selected value of the A-V interval at (194) to reflect the measured current value of the A-V interval. In some examples, processor 80 may update the selected value of the A-V interval by replacing the selected value of the A-V interval with the measured current value of the A-V interval.

In some examples, the measured current value of the A-V interval is a first measured current value. In this example, while CRT is still suspended, processing circuitry 80 may then measure a second current value of the A-V interval, and determine whether the second measured current value of the A-V interval is within the predetermined range. If the second measured current value of the A-V interval is within the predetermined range, then processing circuitry 80 may replace the measured first measured current value of the A-V interval with the selected value of the A-V interval at (194), thereby reverting back to the value stored in the table prior to the measurement of the first current value. In still other examples, processing circuitry 80 may also update other values of the A-V interval associated with the determined heart rate at (194), based on the determination that the current value of the A-V interval is not within the predetermined range.

In addition, upon updating one or more selected values of the A-V interval associated with the determined heart rate, processing circuitry 80 may also update one or more values of A-V intervals associated with other heart rate values stored in one or more of HR/A-V tables 72. For example, upon updating one or more values of the A-V interval associated with the determined heart rate in table 74, processing circuitry 80 may update one or more values of one or more A-V intervals associated with other heart rate values in table 74. The updated values may include all of the values of the A-V intervals stored in table 74, or, in some examples, may include only values of the A-V intervals associated with heart rate values within a predetermined range of the determined heart rate. In the latter example, if the determined heart rate was 80 bpm, then processing circuitry 80 may update one or more A-V interval values associated with heart rate values in a range of, e.g., 80±10 bpm, although other ranges are contemplated. In other examples, processing circuitry 80 may update one or more values of one or more A-V intervals associated with other heart rate values stored in other tables 72.

In some examples, processing circuitry 80 may update one or more values of A-V intervals associated with other heart rate values by adjusting the values of the A-V intervals associated with the other heart rate values by a predetermined value. In some examples, the predetermined value may be the difference between a measured current value of an A-V interval and the value of the selected A-V interval associated with the determined heart rate. In some examples, the predetermined value may be the same for each of the values of the A-V intervals associated with the other heart rate values. In other examples, the predetermined value may vary depending upon, e.g., the magnitude of the difference between the determined heart rate and a heart rate value associated with the values of the other A-V intervals to be updated. In examples in which processing circuitry 80 updates values associated with A-V intervals in more than one of tables 72, the predetermined value by which processing circuitry 80 updates a given value of an A-V interval may depend at least partly upon the identity of the table 72 to be updated.

Various aspects of the techniques may be implemented within one or more processing circuitries, including one or more microprocessors, DSPs, ASICs, FPGAs, or any other equivalent integrated or discrete logic circuitry, as well as any combinations of such components, embodied in external devices, such as physician or patient external devices, electrical stimulators, or other devices. The term "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processing circuitries, such as one or more DSPs, ASICs, FPGAs, general purpose microprocessors, or other equivalent integrated or discrete logic circuitry. Accordingly, the term "processing circuitry," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external device, a combination of an 1 MB and external device, an integrated circuit (IC) or a set of ICs, and/or discrete electrical circuitry, residing in an IMD and/or external device.

Various aspects of the disclosure have been described. These and other aspects are within the scope of the following claims.

The invention claimed is:

1. A system for controlling delivery of cardiac resynchronization therapy (CRT), the system comprising:
therapy delivery circuitry configured to deliver cardiac resynchronization pacing therapy to a heart of a patient;
sensing circuitry configured to sense electrical activity of the heart;
memory circuitry configured to store, in association with each of a plurality of heart rates, at least one respective value for an interval between an atrial event and a ventricular event; and
processing circuitry configured to:
determine the heart rate of a patient based on the electrical activity sensed by the sensing circuitry;
select one of the stored values for the interval between the atrial event and the ventricular event associated with the determined heart rate; and
determine whether to control the therapy delivery circuitry to deliver fusion pacing or biventricular pacing based on the selected one of the stored values for the interval between the atrial event and the ventricular event; and
wherein the memory circuitry is configured to store, in association with each of the plurality of heart rates, a respective value for each of a first interval between an intrinsic atrial event and the ventricular event and a second interval between a paced atrial event and the ventricular event, and wherein the processing circuitry is configured to:
determine whether an atrial event for the current cardiac cycle was intrinsic or paced; and
select either the value for the first interval or the value for the second interval based on the determination.

2. A system for controlling delivery of cardiac resynchronization therapy (CRT), the system comprising:
therapy delivery circuitry configured to deliver cardiac resynchronization pacing therapy to a heart of a patient;
sensing circuitry configured to sense electrical activity of the heart;
memory circuitry configured to store, in association with each of a plurality of heart rates, at least one respective value for an interval between an atrial event and a ventricular event; and
processing circuitry configured to:
determine the heart rate of a patient based on the electrical activity sensed by the sensing circuitry;
select one of the stored values for the interval between the atrial event and the ventricular event associated with the determined heart rate; and
determine whether to control the therapy delivery circuitry to deliver fusion pacing or biventricular pacing based on the selected one of the stored values for the interval between the atrial event and the ventricular event; and
wherein the processing circuitry is configured to:
compare the selected one of the stored values for the interval to a threshold value;
control the therapy delivery circuitry of the implantable medical device system to deliver fusion pacing in response to the selected one of the stored values being less than the threshold value; and
control the therapy delivery circuitry of the implantable medical device system to deliver biventricular pacing in response to the selected one of the stored values being greater than the threshold value.

3. A system for controlling delivery of cardiac resynchronization therapy (CRT), the system comprising:
therapy delivery circuitry configured to deliver cardiac resynchronization pacing therapy to a heart of a patient;
sensing circuitry configured to sense electrical activity of the heart;
memory circuitry configured to store, in association with each of a plurality of heart rates, at least one respective value for an interval between an atrial event and a ventricular event; and
processing circuitry configured to:
determine the heart rate of a patient based on the electrical activity sensed by the sensing circuitry;
select one of the stored values for the interval between the atrial event and the ventricular event associated with the determined heart rate; and
determine whether to control the therapy delivery circuitry to deliver fusion pacing or biventricular pacing based on the selected one of the stored values for the interval between the atrial event and the ventricular event; and
wherein the processing circuitry is further configured to periodically:
determine the heart rate of the patient;
select one of the stored values for the interval between the atrial event and the ventricular event associated with the determined heart rate;
control the therapy delivery circuitry to suspend the delivery of CRT;
while the delivery of CRT is suspended, measure a current value of the interval between the atrial event and the ventricular event;
compare the current value of the interval to the selected value of the interval; and
update at least the selected value of the interval associated with the determined heart rate in the memory based on the comparison.

4. The system of claim 3, wherein the period at which the processing circuitry suspends the delivery of CRT, while the delivery of CRT is suspended, measures the current value of the interval between the atrial event and the ventricular event, compares the current value of the interval to the selected value of the interval, and updates at least the selected value of the interval associated with the determined heart rate in the memory based on the comparison is approximately one hour.

5. The system of claim 3, wherein the processing circuitry is configured to:
determine whether the current value of the interval is within a predetermined range of the selected value, and update at least the selected value of the interval in the memory in response to determining that the current value of the interval is not within the predetermined range of the selected value.

6. The system of claim 3, wherein the processing circuitry is configured to replace the selected value with the current value.

7. The system of 3, wherein the current value comprises a first current value for a first cardiac cycle, and wherein the processing circuitry is configured to:
while the delivery of CRT is suspended, measure a second current value of the interval between the atrial event and the ventricular event for a second cardiac cycle;
compare the second current value of the interval to the selected value of the interval;
determine that the second current value is within a predetermined range of the selected value; and
replace the first current value with the selected value in association with the heart rate in the memory based on the determination.

8. The system of claim 3, wherein the processing circuitry is configured to:
determine a difference between the selected value and the current value; and
update other values of the interval associated with other heart rates based on the difference.

9. A system for controlling delivery of cardiac resynchronization therapy (CRT), the system comprising:
therapy delivery circuitry configured to deliver cardiac resynchronization pacing therapy to a heart of a patient;
sensing circuitry configured to sense electrical activity of the heart;
memory circuitry configured to store, in association with each of a plurality of heart rates, at least one respective value for an interval between an atrial event and a ventricular event; and
processing circuitry configured to:
determine the heart rate of a patient based on the electrical activity sensed by the sensing circuitry;
select one of the stored values for the interval between the atrial event and the ventricular event associated with the determined heart rate; and
determine whether to control the therapy delivery circuitry to deliver fusion pacing or biventricular pacing based on the selected one of the stored values for the interval between the atrial event and the ventricular event; and
wherein the at least one respective value for the interval between the atrial event and the ventricular event comprises a first value for the interval associated with a waking state of the patient and a second value of the interval associated with a sleeping state of the patient.

10. The system of claim 9, wherein the first value of the interval is associated with a resting state of the patient and the at least one respective value further comprises a third value of the interval associated with an exercising state of the patient.

11. An implantable medical device (IMD) configured to deliver cardiac resynchronization therapy (CRT) to a patient, the IMD comprising:
a housing configured for implantation within the patient;
therapy delivery circuitry disposed within the housing and configured to deliver cardiac resynchronization pacing therapy to a heart of the patient;
sensing circuitry disposed within the housing and configured to sense electrical activity of the heart;
memory circuitry disposed within the housing and configured to store, in association with each of a plurality of heart rates, at least one respective value for an interval between an atrial event and a ventricular event; and
processing circuitry disposed within the housing and configured to:
determine a first heart rate of the patient for at least one preceding cardiac cycle based on the sensed electrical activity;
select one of the stored values for the interval between the atrial event and the ventricular event associated with the determined heart rate; and
determine whether to control the therapy delivery circuitry to deliver fusion pacing or biventricular pacing for a current cardiac cycle based on the selected one of the stored values for the interval between the atrial event and the ventricular event, wherein the processing circuitry is further configured to periodically, the period being greater than a cardiac cycle:
determine a second heart rate of the patient based on the sensed electrical activity;
select one of the stored values for the interval between the atrial event and the ventricular event associated with the determined heart rate;
suspend the delivery of CRT;
while the delivery of CRT is suspended, measure a current value of the interval between the atrial event and the ventricular event;
compare the current value of the interval to the selected value of the interval; and
update at least the selected value of the interval associated with the determined heart rate in the memory based on the comparison.

* * * * *